(12) United States Patent
Threlfall

(10) Patent No.: US 11,135,124 B2
(45) Date of Patent: Oct. 5, 2021

(54) EXTERNAL STRUCTURAL BRACE APPARATUS

(71) Applicant: John Threlfall, Volcano, HI (US)

(72) Inventor: John Threlfall, Volcano, HI (US)

(*) Notice: Subject to any disclaimer, the term of this patent is extended or adjusted under 35 U.S.C. 154(b) by 467 days.

(21) Appl. No.: 15/888,041

(22) Filed: Feb. 4, 2018

(65) Prior Publication Data
US 2018/0168910 A1 Jun. 21, 2018

Related U.S. Application Data

(63) Continuation-in-part of application No. 14/326,242, filed on Jul. 8, 2014, now Pat. No. 9,918,892, which
(Continued)

(51) Int. Cl.
*A61H 3/00* (2006.01)
*A61H 3/04* (2006.01)
(Continued)

(52) U.S. Cl.
CPC .............. *A61H 3/008* (2013.01); *A61F 5/02* (2013.01); *A61H 3/00* (2013.01); *A61H 3/04* (2013.01); *A61G 5/025* (2013.01); *A61G 5/122* (2016.11); *A61G 5/124* (2016.11); *A61G 5/125* (2016.11); *A61G 5/128* (2016.11); *A61H 2003/007* (2013.01); *A61H 2201/0157* (2013.01);
(Continued)

(58) Field of Classification Search
CPC . A61H 3/00; A61H 3/008; A61H 3/04; A61H 2003/007; A61H 2003/0205–0216; A61H 2201/0157; A61H 2201/0192; A61H 2201/1253; A61H 2201/1619–1633; A61H 2201/1635; A61H 2201/1642; A61H 2201/1652; A61H 2201/1676; A61H 2203/0425–0431; A61G 5/00; A61G 5/02–026; A61G 5/122; A61G 5/124; A61G 5/125; A61G 5/128; A61F 5/02
See application file for complete search history.

(56) References Cited

U.S. PATENT DOCUMENTS

| | | | | |
|---|---|---|---|---|
| 1,307,058 A | * | 6/1919 | McGrath | A61H 3/04 297/5 |
| 3,467,116 A | * | 9/1969 | Ringewaldt | A45B 3/00 294/100 |

(Continued)

*Primary Examiner* — Keri J Nelson
*Assistant Examiner* — Michelle J Lee
(74) *Attorney, Agent, or Firm* — Roger A. Jackson

(57) ABSTRACT

An external structural brace apparatus for supporting a user in a semi standing position on a surface includes first and second support extension beams that to attach to the surface, also included is a channel having a base with first and second legs, wherein the first and second legs extend in the same direction from opposing sides of the base, the first leg is affixed to the first support structure and the second leg is affixed to the second support structure, the channel can be lockably positioned along the first and second beams. In addition, a saddle seat with a midpoint extension portion, the saddle is attached between the first and second legs and positioned such that the midpoint extension extends opposite of the base, wherein operationally the user partially rests their buttocks on the saddle and leans their back against the base to assume a semi supported standing posture.

5 Claims, 15 Drawing Sheets

Related U.S. Application Data is a continuation-in-part of application No. 13/938,188, filed on Jul. 9, 2013, now Pat. No. 9,226,867.

(51) Int. Cl.
  *A61F 5/02* (2006.01)
  *A61G 5/12* (2006.01)
  *A61G 5/02* (2006.01)

(52) U.S. Cl.
  CPC ........... *A61H 2201/0192* (2013.01); *A61H 2201/1253* (2013.01); *A61H 2201/163* (2013.01); *A61H 2201/1621* (2013.01); *A61H 2201/1633* (2013.01); *A61H 2201/1635* (2013.01); *A61H 2201/1642* (2013.01); *A61H 2201/1652* (2013.01); *A61H 2201/1676* (2013.01); *A61H 2203/0431* (2013.01)

(56) References Cited

U.S. PATENT DOCUMENTS

| | | | | |
|---|---|---|---|---|
| 4,211,426 A | * | 7/1980 | Motloch | A47D 13/04 280/87.041 |
| 5,527,248 A | * | 6/1996 | Crivello | A61H 1/0292 482/96 |

\* cited by examiner

EXTERNAL STRUCTURAL BRACE APPARATUS

RELATED APPLICATIONS

This is a continuation in part (CIP) patent application of U.S. patent application Ser. No. 14/326,242 filed on Jul. 8, 2014 by John Threlfall of Volcano, Hi., US., that is a continuation in part (CIP) patent application of U.S. patent application Ser. No. 13/938,188 filed on Jul. 9, 2013 by John Threlfall of Volcano, Hi., US that is now U.S. Pat. No. 9,226,867 issued on Jan. 5, 2016.

TECHNICAL FIELD OF INVENTION

The present invention generally relates to a portable external structural exoskeleton apparatus utilized typically by an article for bracing and strengthening of the article. More particularly, the present invention helps maintain the structural relationship and integrity between the upper, middle, or lower body structures, in addition to restricting over extension of these body structures in an effort to minimize stress and potential injury to the individual's torso and limbs. Further, more particularly, the present invention provides an active, portable, and lightweight exoskeleton support apparatus that can be worn for long periods of time to assist an individual in performing repetitive high load movements involving stress to the structural portion of an individual's torso and limbs for activities that can include bending, lifting, and standing for extended periods of time.

BACKGROUND OF THE INVENTION

The medical profession may recommend the use of an individual with a back injury or potential back problem to use an exoskeleton structural support apparatus to alleviate the strain and provide relief to the back. The apparatus can immobilize and support the spine when there is a condition that needs to be treated. Depending on the apparatus used, it can put the spine in a neutral, upright, hyper-extended, flexed, or lateral-flexed position. An exoskeleton structural support apparatus can be used to control pain, lessen the chance of further injury, allow healing to take place, compensate for muscle weakness, or prevent or correct a deformity. They offer a safe, relatively inexpensive, non-invasive way to prevent future problems or to help an individual heal from a current condition. The use of exoskeleton structural support apparatus which are commonly termed "braces" is widely accepted and is an effective tool in the treatment of back disorders. In fact, more than 99% of orthopedic physicians advocate using braces as there is a high potential benefit and little downside risk of the individual wearing the brace. In fact, historically braces have been used as far back as 2000 B. C. Recently, braces have become a popular way to help prevent primary and secondary lower back pain from ever occurring or reoccurring.

The Occupational Safety & Health Administration (OSHA) cites injuries to the upper, middle, and lower back as the most common reason for absenteeism in the general workforce after the common cold. It is estimated that about 80% of adults in North America can expect a back injury in their lifetime and about 10% can expect a re-injury. Back injuries can develop gradually as a result of micro-trauma brought about by repetitive activity over a period time or a single traumatic event. Back injuries can be the immediate result of improper lifting techniques and/or lifting loads that are too heavy for the back to support or brought on by repetitive lifting of lighter loads.

While an acute injury may seem to be caused by a single well-defined incident, OSHA states that the actual cause can be from a series of micro traumas coupled by years of weakening of the muscular-skeletal support system by repetitive lifting and bending, being the most hidden type of injury. Injuries can arise in muscles, ligaments, vertebras, and discs, either singly or in combination. Although back injuries do not cause death, they do account for a significant loss in productivity, income, and expenses plus the physical suffering. For some, the pain and suffering is long-term or even lifelong. For individuals with long-term, disabling musculoskeletal injuries, lifetime earnings may drop significantly. These individuals may also suffer a loss of independence due to a restricted ability to ambulate or complete daily tasks such as cooking, cleaning, bathing, dressing, and the like that can lead to a diminished quality of life and depression.

OSHA cites back injuries in the United States as one of the leading causes of workplace absenteeism and disability; it afflicts over 600,000 employees each year with a cost of about $50 billion in lost productivity and medical costs. In addition, one to five percent of this group will suffer chronic back pain that lasts six months or longer. The frequency and economic impact of back injuries on the work force are expected to increase significantly over the next several decades as the age of the working population increases and the cost of healthcare escalates, thus intensifying the problem. For those under the age of 45, back pain is the most frequent cause of activity limitation. Although 80% to 90% of individuals will recover from back pain within three to six days of their injury, the Journal of the American Medical Association estimates that $31 million will be spent on physician office visits and $20 billion on prescription drugs—and only three percent of that total cost will go to prevention of back pain.

Thus, it is clear that there is a great need in the art for an improved method and system for providing active support to the upper, middle, and lower back to assist in bending, lifting, and standing to prevent injury while avoiding the shortcomings and drawbacks of the prior art apparatuses and methodologies as reviewed in the following section.

PRIOR ART

In looking at the high end of the prior art in this area with powered exoskeletons, Lockheed Martin has designed a Human Universal Load Carrier termed an acronym as the HULC being an anthropomorphic exoskeleton robot for soldiers carrying heavy combat loads that increase the stress on the body leading to potential injuries. With the Lockheed Martin wearable exoskeleton robot, these loads are transferred to the ground through powered titanium legs without loss of mobility. The Lockheed Martin HULC is a completely un-tethered, hydraulic-powered anthropomorphic exoskeleton that provides individuals with the ability to carry loads of up to 200 lbs for extended periods of time and over all terrains. The flexible design of the Lockheed Martin allows for deep squats, crawls and upper-body lifting. The Lockheed Martin exoskeleton fits individuals from 5'4" to 6'2" and weighs approximately 53 pounds. The Lockheed Martin exoskeleton senses what users want to do and where they want to go in addition to augmenting their ability, strength and endurance. An onboard micro-computer ensures the Lockheed Martin exoskeleton moves in concert with the individual. The Lockheed Martin modularity allows for major components to be swapped out in the field, in addition to having a unique power-saving design for the user to operate on battery power for extended missions.

Also in this same area Berkley Bionics has designed an eLEGS exoskeleton that has an emphasis on helping paraplegics walk, having the same root design team that developed the HULC as previously described, having a lot of the same design methodology in using battery powered hydraulics. However, both the HULC and the eLEGS are both currently in the developmental prototyping stage having a cost of about $100,000 per unit, with a likely potential of a price reduction to $50,000 for a simplified version, thus still being an esoteric technology for now.

Now looking considerably back in time at the prior art, toward simpler non-powered exoskeleton apparatus that utilize springs, wire, and elastomeric components as assistive exoskeletons, starting with U.S. Pat. No. 654,173 to Mendenhall discloses a back-brace for cotton pickers or any activity requiring a repetitive stooping posture. In Mendenhall the apparatus is attached to the individual's shoulders, waist, and limbs, and uses wire interconnected between flexible elastic fabric straps which press against the individual's lower portion of their back, being connected to the user's shoulders and upper legs, exerting a resistive support for the lower back, see FIG. 1, items 1, 3, 5, and 14, particularly when the user is bending or stooping over. Two major problems with Mendenhall are that it requires additional effort from the user to do the initial bending or stooping over as the wires 16 will limit the amount of bending over that can be done, and further to this the wire 16 with the attachment point on the user's shoulders and upper legs acts to put the user's back into added compression, thus the exoskeleton in Mendenhall does not itself carry any of the user's load, it simply transfers the load to the added compressive force upon the user's back, which is undesirable.

Similar to Mendenhall, in Vigne being in U.S. Pat. No. 1,544,162 discloses a set of more than 15 adjustable straps that attach to the shoulders, waist, hips, and knees of the user, wherein these attachment straps are interconnected with coiled springs 13, 17, and 8, as shown in FIGS. 1 and 2, that urge the straps toward one another, thus again as in Mendenhall when the user bends over there is resistance and then in an opposing manner then coiled spring urges the user into an erect standing position. However, much the same as Mendenhall, the coiled springs put compressive stress upon the back of the user which is undesirable and the exoskeleton carries absolutely no weight or load itself, as the flexible straps and coiled springs apparatus of Vigne has no independent stiffness of its own and thus does not remove any load from the user's bone structure and even worse both Mendenhall and Vigne further increase the compressive force loading on the user's back, thus in effect leaving the user worse off than if they did not use the Mendenhall or Vigne apparatus at all.

Also somewhat like Mendenhall and Vigne, however, a bit of improvement due to the coil spring providing lateral bending resistance with tensile resistance, in U.S. Pat. No. 1,202,851 to Kelly disclosed a back brace with an elongated bar twisted between its ends into a coil spring with an adjustable mounted pad designed to rest against the lower back thereby connecting at its opposing ends to the shoulder and the upper legs of the user, see FIG. 1. In Kelly each end of the rod has padded grips and is connected to the rod by adjustable couplings. One Y-shaped padded bar in Kelly extends over the shoulders while a second y-shaped bar is used to attach the upper thighs to the support apparatus. Kelly attaches to the upper body and thighs using no fasteners and is used to lightly and support an individual bending at the hips. In addition, Kelly does not offer a means to adjust the amount of support offered by the apparatus. Thus as differentiated as against Mendenhall and Vigne, Kelly does not solely rely upon a wire or coiled spring to urge the user into an erect position via only tensile pulling along a longitudinal axis of the wire or coiled spring, with Kelly at least recognizing the problem of needing lateral stiffness (being perpendicular to the wire or coiled spring longitudinal axis) as being required for the exoskeleton to actually carry some of the user's load. However, Kelly still has a component of longitudinally based tensile contracting force due to the coil spring, and thus can still put the user's back in undesirable compression, thus having the same drawbacks as Mendenhall and Vigne in that area as previously described.

Finally in getting away from the wire or coiled spring that exerts pulling tension along its longitudinal axis, Williamson uses a multi plate leaf type spring 2, as disclosed in U.S. Pat. No. 1,409,326 wherein the leaf spring 2, as shown in FIGS. 1 and 2, does not induce longitudinally based pulling tension on its own, which is highly desirable as not independently inducing a compressive loading upon the back. Functionally overall Williamson is much like Mendenhall, Vigne, and Kelly and includes a spring lift apparatus which when worn by an individual will assist individual in repeated bending over and stooping to relieve lower back strain. Further, the Williamson apparatus assists an individual in raising the upper body to an erect position while allowing the individual to temporarily sit while wearing the apparatus. The Williamson apparatus is strapped to the individuals head, upper chest, and knee for support, see FIG. 2 items 5, 6, 17 and 18 and FIG. 1 items 10, 12, 13, and 14.

In addition, Williamson is strapped to the individual's head, shoulders, one leg, and shovel, also including a fixed setting for support and resistance, see FIG. 2 17, 18 and FIG. 1 items 10, 12, 13, and 14. The Williamson apparatus provides unbalanced asymmetrical support to the back by strapping itself to only one leg of an individual, as the asymmetrical attachment to the individual creates unequal support for the left and right lower back. A further problem in Williamson is in the racket 10 and setscrew 11 as shown in FIG. 2, wherein with the user stooped over there is a locked longitudinal arrangement as between the bracket 10 and the rigid extension 4 that in effect will produce the undesirable effect of again compressing the back of the user as when the bend or stoop over extension 4 will pull downward compressing the back, thus again bringing on the same problems as previously described in Mendenhall, Vigne, and Kelly in that area as previously described, thus due to the bracket 10 and the setscrew 11 completely takes away the benefit of the leaf spring 2 as also previously described.

Finally, the next reference to Naig in U.S. Pat. No. 3,570,011 does a better job of not compressing the user's back by using a beam 12 that pivots upon the user's lower back to simply pull against the user's upper chest in a manner completely perpendicular to the user's back, however, adding the somewhat undesirable issue of putting the user's lower back and legs into compression, which probably being better than putting the user's back into compression via elastic straps 52, whereas straps 44 are not stretchable, thus even this compression is still not desirable, further Naig is quite large and bulky, especially due to tubular frame 12, see in particular FIG. 2. In detail, Naig is comprised of a series of ropes, straps, buckles and harnesses used to attach the apparatus to individual's chest, waist, hips, ankles and feet, see FIG. 1 items 10, 12, 14, 16, 20, 26, 30, 34, 36, 44 and 57.

In an opposite approach, Deamer in U.S. Pat. No. 4,829,989 is mounted on the user's front or chest side as opposed to all the previously described references that have the exoskeleton apparatus mount on the back side of the user, thus again recognizing the problem of avoiding compressive force upon the user back, that was somewhat recognized by Naig, Williamson, and Kelly. Thus Deamer is pushing with force against the user's chest and the front of the user's legs wherein slidable pads 32 and 36 help preclude compressive force to be placed upon the user's back, which the Deamer apparatus urges the user into an upright position. Deamer is a portable spring leveraged apparatus that attaches to the individual's hips to offset the strain to the hips while stooping.

The Deamer apparatus includes a U-shaped frame, hinged in each arm of the U and provided with spring urging at each hinge point, see FIG. 2 items 32 and 40. The Deamer frame is belt mounted at the individual's waist with the hinge points adjacent the hips and with the bottom of the U and arms providing padded slidable contact at the individual's chest and thighs, respectively, see FIG. 1, items 22, 28, 32, 36, 34, and 40. In Deamer the two arms 46 provide independent leg movement for walking while the chest contact 32 resiliently supports the upper torso weight during leaning and stooping. The Deamer apparatus only provides one way support and restraint to the lower back when an individual bends forward and does not provide support for bending backward.

Further, having much the same design and drawbacks as Vigne, in U.S. Pat. No. 6,190,342 to Taylor, disclosed a back harness for the alleviation of individual's back strain using multiple elastic straps than run longitudinally along the user's legs and back, see FIG. 2A and FIG. 2B, wherein undesirably again the user's back is put into compression from the elastics 19, 21, and 45. The Taylor harness provides urging from the shoulders to the lower back and legs if the user into the upright position and provides light assistance in lifting medium weight objects, however, as in Vigne, Taylor provide absolutely no rigidity on its own. Taylor provides the upright urging from the shoulders to the lower back using soft elastic straps 19, 21, and 45. Taylor requires the individual to install and wear a cumbersome number of straps buckled to the torso, shoulders, upper back, mid torso, upper legs, mid-legs, ankles and feet.

Continuing in this area in the prior art in the U.S. Pat. No. 6,450,131 to Broman which is similar to Mendenhall discloses a light flimsy harness for supposedly preventing lower back injuries caused by improper bending and lifting however, again as in Mendenhall, the user's back is put undesirably into compression from the user bending over or stooping and also as in Mendenhall the Broman apparatus has no independent stiffness with which to support any weight or load. In Broman the harness consists of a thin, light weight flexible back strap 26 and two flexible shoulder straps 28 as shown in FIG. 2. The Broman harness and straps are used to allow forward bending of the lower back and an individual's knees. In Broman two additional straps 38 compose the lower portion of this apparatus that are connected to the back 26 and shoulder 28 straps, with the lower left strap has one end connected to the left foot, while the lower right strap has one end connected to the right foot, see FIG. 2.

Yet further in the prior art in the U.S. Pat. No. 7,553,266 to Abdoli, being fairly like Naig discloses a lift assist apparatus and method, however, being worse than Naig in that the user's back is put into undesirable compression via elastic member 40, 50, 60 and 70 as shown in FIG. 1, as opposed to Naig who used a rigid member 12 to pivot upon the user's lower back thus inducing a force perpendicular to the user's back, wherein Abdoli pulls the user's shoulders toward the lower back in order to urge the user in an upright position, thus putting the user's back into the undesirable compression, and further also undesirably putting the user's legs into compression. Abdoli includes two anchors that attach to the sides of the individual's body joints and elastic straps connecting the first anchor and the second anchor to the individual's torso, see FIG. 1 items 5, 20, 25, 30 and 35. The Abdoli apparatus may be used at an individual's waist, ankle, wrist, knee, hip, elbow, shoulder, and/or at least one joint of the back and/or neck. In Abdoli, articulation of the individual's joint in a first direction causes deformation of the elastic member and storing of energy, and articulation of the joint in a second direction causes relaxation of the elastic member wherein the energy is released and assists the individual to perform a motion in said second direction. The Abdoli system uses soft fabric and elastic straps to passively support an individual's back. The passive support is adjustable by loosening and tightening the fabric straps, noting that as previously discussed in Mendenhall, Vigne, Taylor, and Broman, Abdoli has no independent rigidity to remove any load from the user.

Moving to very narrow and specific purpose exoskeleton apparatus in the prior art in U.S. Pat. No. 4,638,510 to Hubbard, disclosed is a head and neck restraint apparatus for use in a high performance vehicle, see FIG. 1 and in particular straps 15 a, 15b, and 15c, further in FIG. 3. The primary function of Hubbard is to protect the head and neck positional relationship upon impact, thereby helping to prevent hyper extending neck injury upon a frontal impact. The Hubbard apparatus includes a tether strap attached between the vehicle and the helmet, wherein the tether provides the individual's restraint. The Hubbard apparatus is used in conjunction with a harness seat assembly that affixes the individual's head and neck to the vehicles seat via the helmet to help restrict movement. The Hubbard apparatus is very specific in only protecting the head and neck positional relationship and makes no attempt to protect the upper, middle or lower back when bending, lifting, standing and pushing.

In looking at specifically the use of stiffening flex rods as they are currently applied to exercise machines in the prior art, in U.S. Pat. No. 4,620,704 to Shefferaw, relating to an exercising machine having a plurality of different cross sectional diameter resilient rods which are flexed laterally (i.e. perpendicular to their longitudinal axis) and resist movement of an individual using the exercise machine via cables, see FIG. 12 and FIG. 13, items 44 and 52. In Shefferaw '704 forces are exerted on the resilient rods through cables to which a variety of attachments such as hand grips, foot stirrups, and a sliding bench can be connected to exercise different parts of the body. The rods in Shefferaw '704 can be used in any combination to suit the requirements and physical abilities of the person using the machine.

Shefferaw '704 contains the plurality of vertically extending rods of resilient material mounted on a post in a cantilevered fashion with the lower ends of the rods being rigidly affixed to the post and the upper ends of the rods being cantilevered freely and selectively connectable to the various cables to the previously mentioned attachments. The Shefferaw '704 apparatus requires the use of distinctive different cross section diameter rods to vary the degree of lateral flexing resistance. The Shefferaw '704 apparatus was designed to stay in a permanent, fixed position and not designed to be carried in a portable manner by an individual. In a second patent to Shefferaw, in U.S. Pat. No. 4,725,057, Shefferaw adds the ability for an individual to collapse the exercising machine for storage and portability to Shefferaw U.S. Pat. No. 4,620,704.

Further, in the prior art in U.S. Pat. No. 5,348,035 to Porter discloses a strap harness assembly that attaches to a pair of crutches, the strap harness encompasses the user's shoulders, waist, and hips for a more complete upper body stability, al for the purpose of reducing weight force loading on the user's arms, wrists, and armpits while using crutches. While the goal in Porter is admirable, the execution is more difficult as the straps have a complicated and extension attach/detach system that is time consuming to use, see FIG. 1 in particular.

Next, in the prior art in U.S. Pat. No. 6,263,892 to Baker, disclosed is a support assembly for a crutch user having a seating portion that is configured somewhat as a swing seat having a wider strap shaped in the form of an "U", see FIG. 3 as an example. This swing type seat in Baker would work best if the user were perched against a wall for lateral support and used the swing seat for vertical stability, the seat strap also has an attachment for adding to lateral stability to the crutch by having an additional strap, see FIGS. 1, 11A, 11B, and 23.

Yet, further, in the prior art in U.S. Pat. No. 4,245,659 to Shofner discloses a crutch assembly that has an upper lateral cross member beam that is configured to attach to a user to do two things, firstly to help support the user's upper torso and to connect the top portions of the crutches together through a rigid lateral beam that allows a ball in socket type restricted omnidirectional movement of the crutches relative to one another. However, in Shofner the crutch omnidirectional movements to one another are not coupled and are totally independent, which could lead to instability.

Also, in the prior art in U.S. Pat. No. 5,605,169 to Light discloses a collapsible walker with a retractable seat having a pair of grasping handles that are pivotally linked to a pair of lockable sliding sleeves on the frame support members to adjust the sear height. Further in Light, the entire frame is collapsible for storage to save space, also wheels are provided on two of the four frame legs to help the user ambulate across a surface.

In addition, in the prior art in United States patent application publication number 2017/0231856 to Karlovich discloses a mobility assistance device that includes first and second frames positioned on left and right sides of the user also having handles on each of the first and second frames with a waist belt disposed between the first and second frames to allow user standing stability without the use of their hands for support via the first and second frames that are also foldable to one another for compact storage. Karlovich further has a fabric panel seat disposed between the first and second frames to convert the device into a transport type wheelchair.

What is needed is an external structural brace apparatus that is practical, affordable, and portable, requires no power to operate, is easy to take on and off, is easily adjustable for varying stiffness and that has the ability to provide rigid user skeletal support without placing compressive loading upon the user's own skeletal structure.

SUMMARY OF THE INVENTION

Broadly the present invention is the external structural brace apparatus for supporting the user in the semi standing position on the surface to relieve shoulder, armpit, hand, foot, and wrist loads, the external structural brace apparatus including the first support extension beam having the first beam proximal end portion and the opposing first beam distal end portion and the first beam longitudinal axis spanning therebetween. The first beam proximal end portion is adapted to attach to the surface, with the first support extension beam including the first support structure that is removably engagable to the first support extension beam along the first longitudinal axis.

Further included in the external structural brace apparatus is the second support extension beam having the second beam proximal end portion and the opposing second beam distal end portion and the second beam longitudinal axis spanning therebetween, the second beam proximal end portion is adapted to attach to the surface, the second support extension beam including the second support structure that is removably engagable to the second support extension beam along the second longitudinal axis.

Also included in the external structural brace apparatus is the channel having the base with the first leg and the second leg, wherein the first and second legs each extend in the same direction from opposing sides of the base, the channel extending lengthwise along the channel lengthwise axis, the first leg is affixed to the first support structure and the second leg is affixed to the second support structure, thereby positioning the first and second longitudinal axes substantially parallel to one another. Further, the first and second beam distal end portions and the first and second beam proximal end portions are on matching ends from one another, wherein operationally the channel can be positioned and locked along the first and second longitudinal axes between the first and second beam distal end portions and the first and second beam proximal end portions.

In addition, included in the external structural brace apparatus is the saddle seat being generally planar with a midpoint substantially planar extension portion, the saddle is attached between the first and second legs and positioned such that the midpoint substantially planar extension extends opposite of the channel base, wherein operationally the user partially rests their buttocks on the saddle and leans their back against the channel base to assume a semi supported standing posture.

REFERENCE NUMBERS IN DRAWINGS

Figure 1:
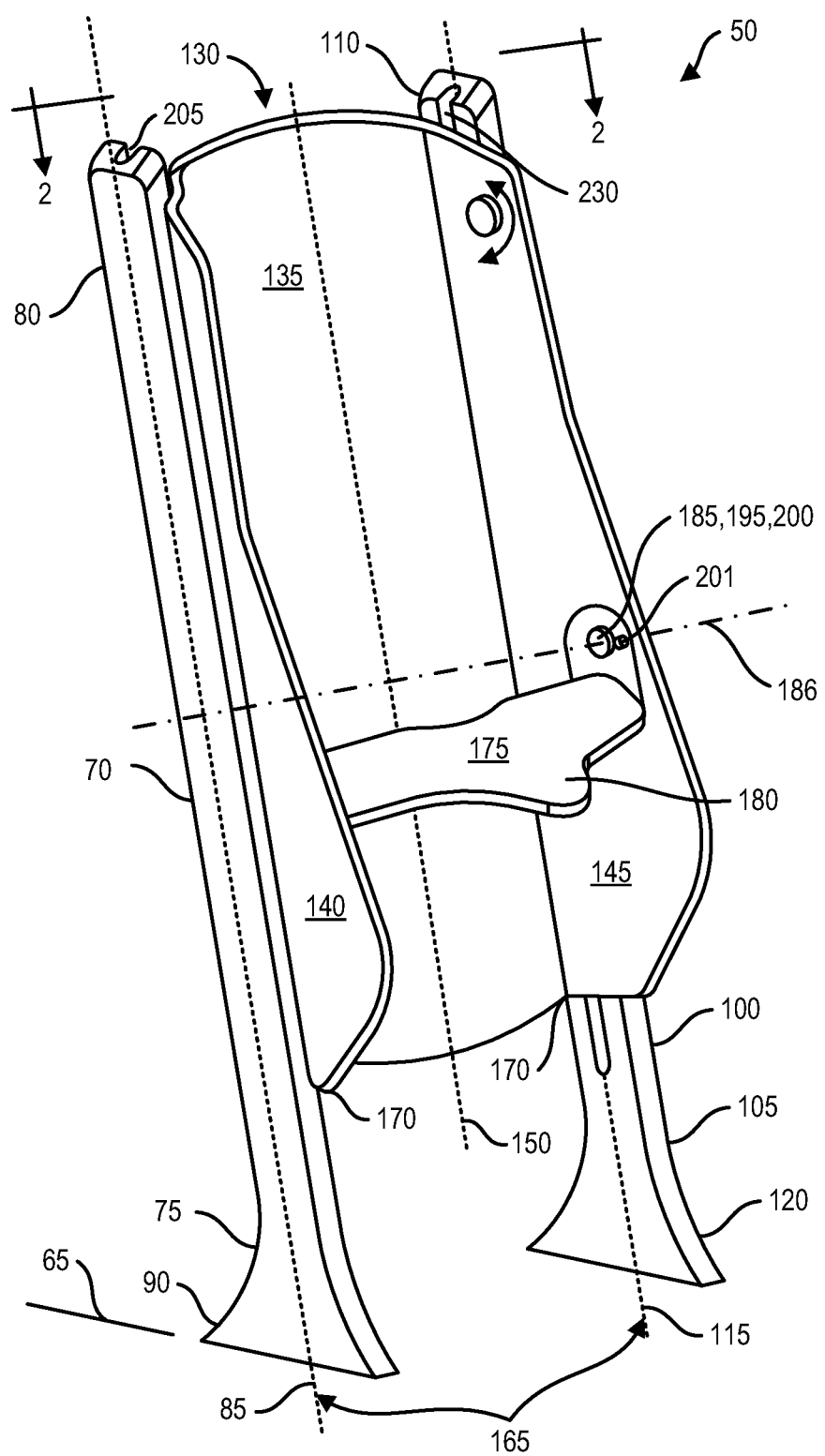
FIG. 1 shows a perspective view of an external structural brace apparatus for supporting a user in a semi standing position on a surface that includes first and second extension beams, a channel, and a saddle seat.

50 External structural brace apparatus
55 User
60 Semi standing/seating supported position of the user 55
65 Surface
70 First support extension beam
75 First proximal end portion of the first support extension beam 70
80 First distal end portion of the first support extension beam 70
85 First longitudinal axis of the first support extension beam 70
90 First proximal end portion 75 adapted to attach to the surface 65
95 First support structure of the first support extension beam 70
100 Second support extension beam
105 Second proximal end portion of the second support extension beam 100
110 Second distal end portion of the second support extension beam 100
115 Second longitudinal axis of the second support extension beam 100
120 Second proximal end portion 105 adapted to attach to the surface 65
125 Second support structure of the second support extension beam 100
130 Channel
135 Base of the channel 130
140 First leg of the channel 130
145 Second leg of the channel 130
150 Channel lengthwise axis
155 First leg 140 affixed to the first support structure 95
160 Second leg 145 affixed to the second support structure 125
165 Substantially parallel position of the first 85 and second 115 longitudinal axes
170 Channel positioned and locked along the first 85 and second 115 longitudinal axes
175 Saddle seat that is generally planar
180 Midpoint substantially planar extension portion of the saddle seat 175
185 Attachment of the saddle seat 175 between the first 140 and 145 second legs
186 Pivot axis of the saddle seat 175
190 First leg mechanism of the saddle attachment 185
195 Second leg mechanism of the saddle attachment 185
200 Pivotal adjustment and lock of the saddle 175 in relation to the first 70 and second 100 support extension beams
201 Lock pin for pivotal adjustment 200
202 Hole for lock pin 201 in attachment 185
203 Hole for lock pin 201 in attachment in first 140 and second 145 legs
204 Locked state for pin 201

205 First slot in the first support extension beam 70
206 Unlocked state for pin 201
210 First slot 205 running parallel to the first longitudinal axis 85
215 First element
220 First free slidable engagement of the first element 215 to the first slot 205
225 First asymmetric locked slidable engagement of the first element 215
226 Locked state rotation of the first element 215 to the first slot 205
227 Unlocked state rotation of the first element 215 to the first slot 205
230 Second slot in the second support extension beam 100
235 Second slot 230 running parallel to the second longitudinal axis 115
240 Second element
245 Second free slidable engagement of the second element 240 to the second slot 230
250 Second asymmetric locked slidable engagement of the second element 240
251 Locked state rotation of the second element 240 to the second slot 230
252 Unlocked state rotation of the second element 240 to the second slot 230
255 Seat belt
260 Attachment of the seatbelt 255 to the first 140 and second 145 legs saddle attachments 185
265 Chest belt
270 Attachment of the chest belt 265 to the first 140 and second 145 legs
300 First alternative embodiment external structural brace apparatus
305 Ambulate along the surface 65
310 Frame structure
315 First end portion of the frame structure 310
320 Second end portion of the frame structure 310
325 Means for ambulating along the surface 65
330 Attachment of the means 325
335 Saddle seat
340 Wide portion of the saddle seat 335
345 Midpoint narrow extension portion of the saddle seat 335
350 Attachment of the saddle seat 335 to the frame structure 310 second end portion 320
355 Torso support ring
360 Attachment of the torso support ring 355 to the frame structure 310 second end portion 320
365 Arcuate extension
370 Emanating of the arcuate extension 365 from the saddle seat 335 narrow extension portion 345
375 First pivotal attachment
380 First pivotal axis
385 First selectable pivot of the saddle seat 335
390 First selectable surface 65 height of the saddle seat 335
395 Arcuate band
400 Affixment of the arcuate band 395 to the first pivotal attachment 375
405 Moving in lockstep of the arcuate band 395 with the saddle seat 335
410 First pivotal movement about the first pivotal axis 380
415 Channel shaped extension
420 Emanating of the channel shaped extension 415 from in-between the saddle seat 335 narrow extension portion 345 and the saddle seat 335 wide portion 340
425 Second pivotal attachment
430 Second pivotal axis
435 Second selectable pivot of the saddle seat 335
440 Second selectable surface 65 height of the saddle seat 335
445 Arcuate hoop
450 Affixment of arcuate hoop 445 to the second pivotal attachment 425
455 Moving in lockstep of the arcuate hoop 445 with the frame structure 310
460 Leg belt
465 Attachment of the leg belt to the channel shaped extension 415
470 Retainer
475 Disposing of the retainer 470 on the saddle seat 335 narrow extension portion 345
500 Second alternative embodiment external structural brace apparatus
505 First support extension strut
510 First strut proximal end portion
515 First strut distal end portion
520 First strut longitudinal axis
525 First strut telescoping cantilever
530 Extension movement of the first strut telescoping cantilever 525
535 Retraction movement of the first strut telescoping cantilever 525
540 Second support extension strut
545 Second strut proximal end portion
550 Second strut distal end portion
555 Second strut longitudinal axis
560 Second strut telescoping cantilever
565 Extension movement of the second strut telescoping cantilever 560
570 Retraction movement of the second strut telescoping cantilever 560
575 Primary pivotal couple
580 Primary pivotal movement
585 Primary radial plane
590 Mechanism
595 Support structure
600 Connection from the support structure 595 to the mechanism 590
605 Support structure that removably engages an upper torso of the user 55
610 Extension element
615 Proximal end of the extension element 610
625 Distal end portion of the extension element 610
630 Segmented links section
635 Midpoint of the segmented links section 630
640 Lower end of the segmented links section 630
645 Pivotal attachment of the distal end 625 to the midpoint 635 of the segmented links section 630
650 Arcuate shape of the segmented links section 630
655 Straight shape of the segmented links section 630
660 Attachment of the segmented links section 630 to the torso of the user 55
665 Attachment of the lower end 640 to legs of the user 55
670 Lockable segmented links section in the straight shape or upright position 655
675 First handle structure
680 Disposing of the first handle structure 675 on the first strut proximal end portion 510
685 Second handle structure
690 Disposing of the second handle structure 685 on the second strut proximal end portion 545

695 Attachment of the saddle seat 335 to the lower end 640 of the segmented links section 630
700 First pivot base
705 First pivot primary end portion
710 First pivot secondary end portion
720 Affixment of the first pivot base to the first strut proximal end portion 510
725 First rotational couple
730 First extension element proximal end
731 Second pivot base
732 Second pivot primary end portion
733 Second pivot secondary end portion
734 Affixment of the second pivot base to the second strut proximal end portion 545
735 First S shaped arm
736 Second rotational couple
737 Second extension element proximal end
740 First principal pivotal connection
745 First dependent pivotal connection
750 Second S shaped arm
755 Second principal pivotal connection
760 Second dependent pivotal connection
765 Sheath
770 Slidable engagement of the sheath 765
775 Opposing lateral movement of the slidable engagement 770
780 Substantially parallel movement 775
785 First handle pivotal engagement
790 First movement along the first strut longitudinal axis 520
795 Pair of first pivotal links
800 Ancillary first strut
805 Extend and retract movement of the ancillary first strut 800
810 First distal link
815 Pivotal link of the ancillary first strut 800 to the first distal link 810 and the first strut distal end portion 515
820 Second handle pivotal engagement
825 Second movement along the second strut longitudinal axis 555
830 Pair of second pivotal links
835 Ancillary second strut
840 Extend and retract movement of the ancillary second strut 835
845 Second distal link
850 Pivotal link of the ancillary second strut 835 to the second distal link 845 and the second strut distal end portion 550
855 Leg belt
860 Attachment of the leg belt 855 to segmented links lower end 640
865 Latch
870 Bar
875 Protrusion of the bar 870
880 Bar pivotal attachment
885 Receiving channel
890 Open state of the bar 870 and the receiving channel 885
895 Closed state of the bar 870 and the receiving channel 885
900 Member that urges the bar 870 and the receiving channel 885 from the open state 890 to the closed state 895

DETAILED DESCRIPTION

Starting with FIG. 1 shown is a perspective view of an external structural brace apparatus 50 for supporting the user 55 in the semi standing position 60 on the surface 65 that includes the first 70 and second 100 extension beams, the channel 130, and the saddle seat 175. Next, FIG. 2 shows view 2-2 from FIG. 1 of the external structural brace apparatus 50 for supporting the user 55 in the semi standing position 60 showing specifically the top plan view of the saddle seat 175 with the midpoint planar extension 180, attachment of the saddle seat 175 185 to the legs 140, 145 of the channel 130 about the pivotal axis 186.

Figure 2:
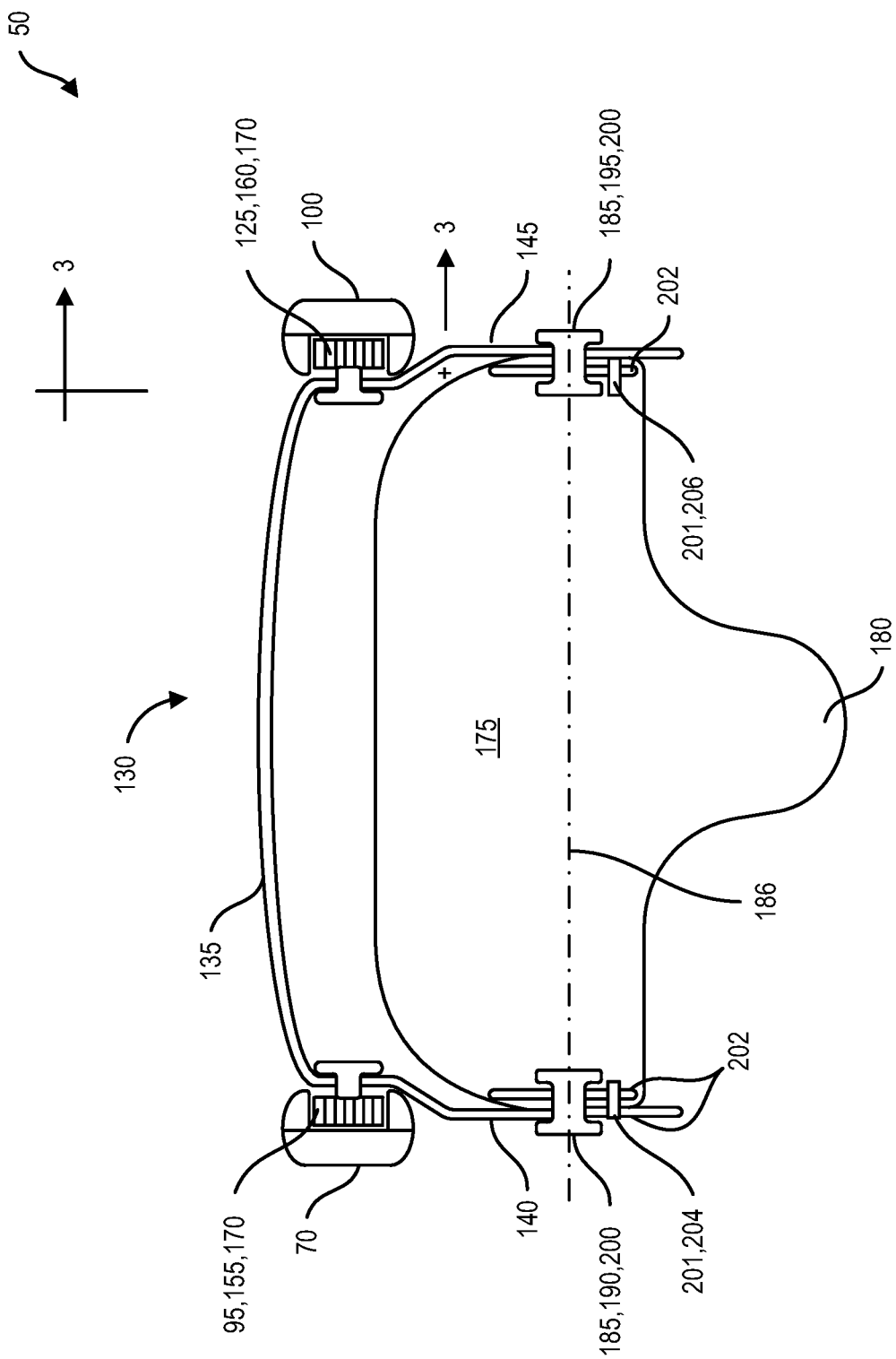
FIG. 2 shows view 2-2 from FIG. 1 of the external structural brace apparatus for supporting a user in a semi standing position showing specifically the top plan view of the saddle seat with a midpoint planar extension, and attachment of the saddle seat to legs of the channel about a pivotal axis.
Figure 3:
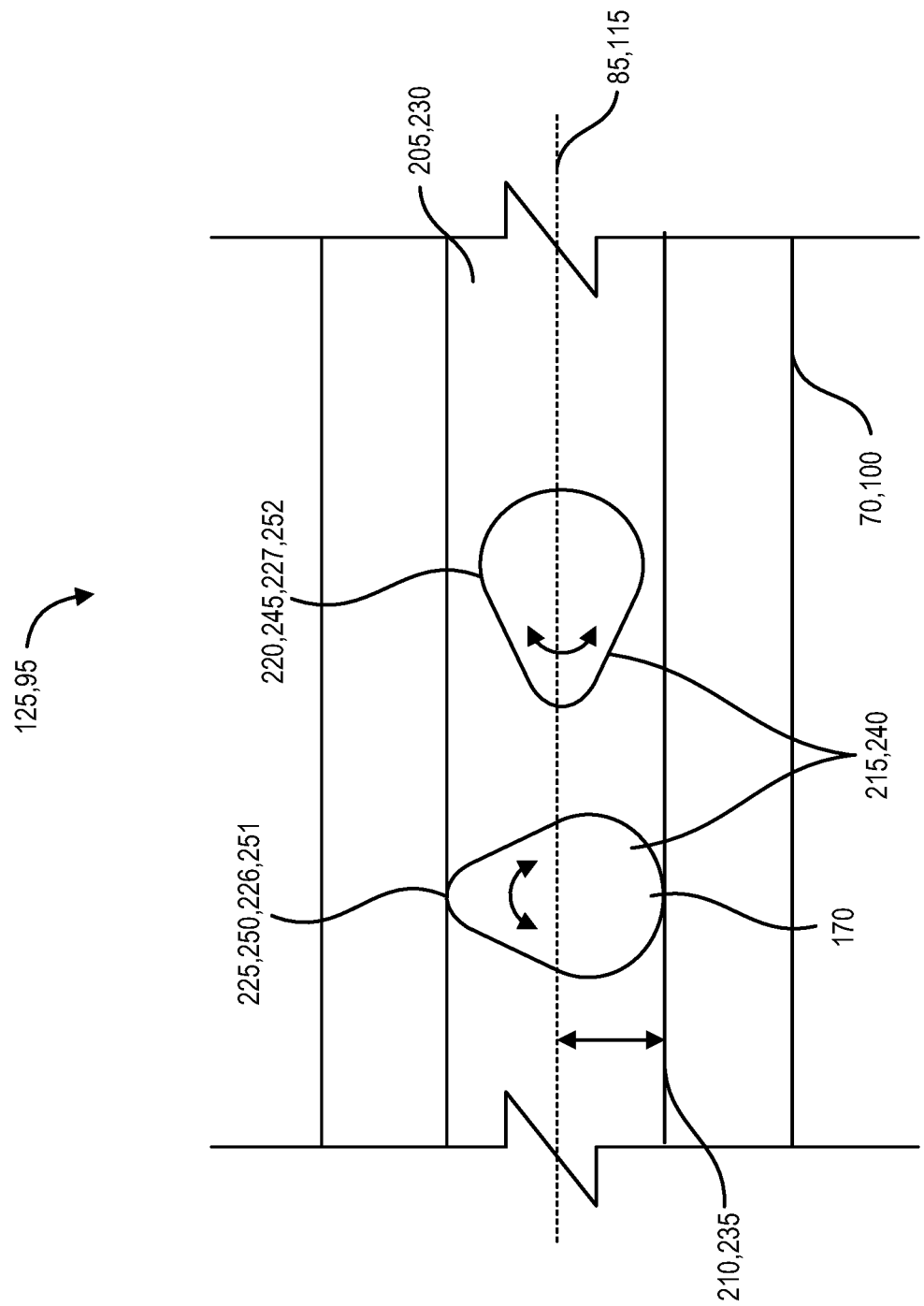
FIG. 3 shows view 3-3 from FIG. 2 of the first and second extension beams showing specifically first and second slots with asymmetric slidable engagements of first and second elements in locked and unlocked states to position the channel along the first and second extension beams.
Figure 4:
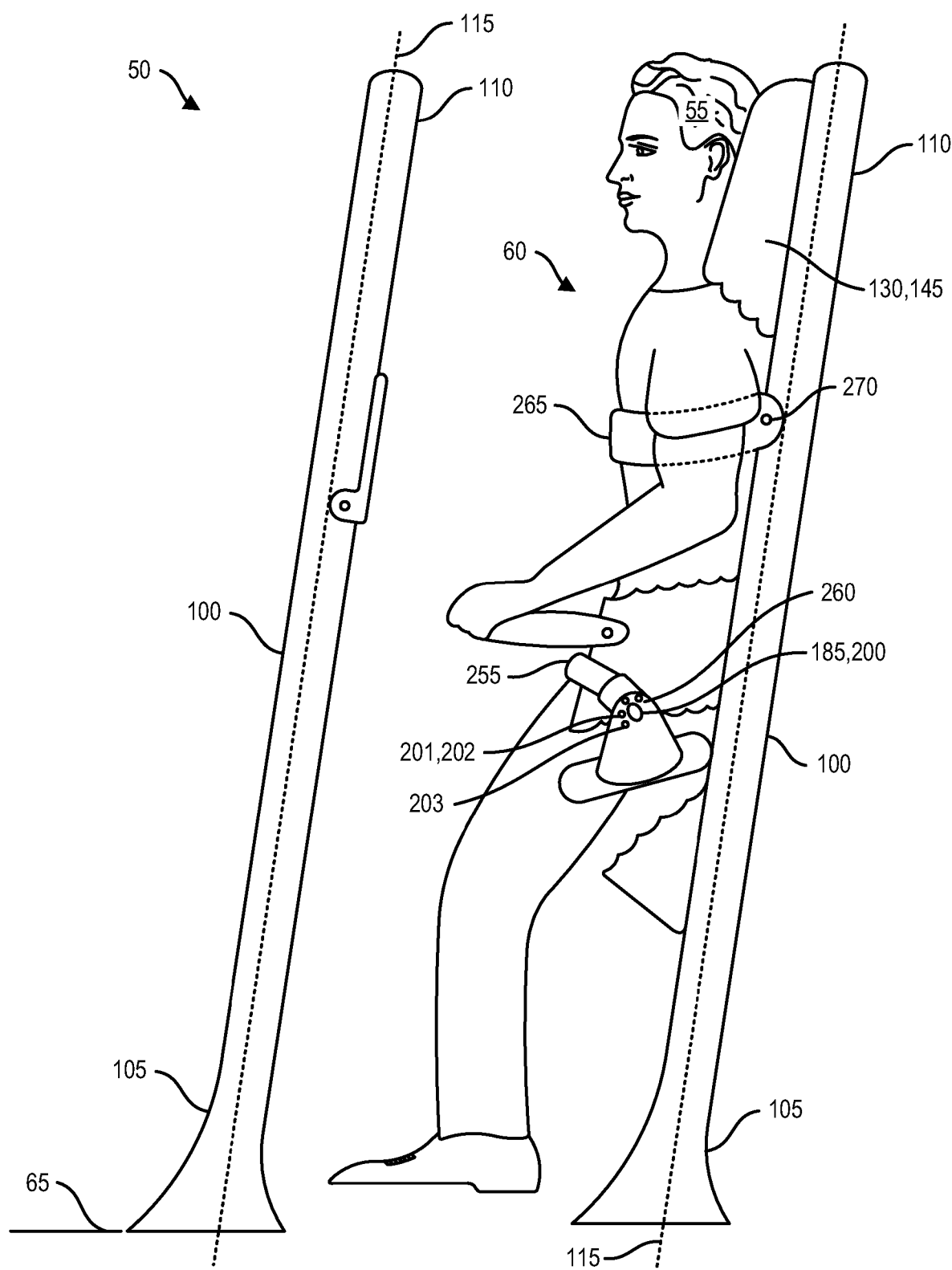
FIG. 4 shows a side elevation view of the external structural brace apparatus for supporting a user in a semi standing position on a surface that further includes a chest belt and a seat belt plus shows a pair of the external structural brace apparatus is positional relation to one another on the surface.

Continuing, FIG. 3 shows view 3-3 from FIG. 2 of the first 70 and second 100 extension beams showing specifically the first 205 and second 230 slots with asymmetric locked slidable engagements of the first 225 and second 250 elements in locked 226, 251 and unlocked 227, 252 states to position the channel 130 along the first 70 and second 100 extension beams. Moving onward, FIG. 4 shows a side elevation view of the external structural brace apparatus 50 for supporting the user 55 in the semi standing position 60 on the surface 65 that further includes the chest belt 265 and the seat belt 255 plus shows a pair of the external structural brace apparatus 50 is positional relation to one another on the surface 65.

Figure 5:
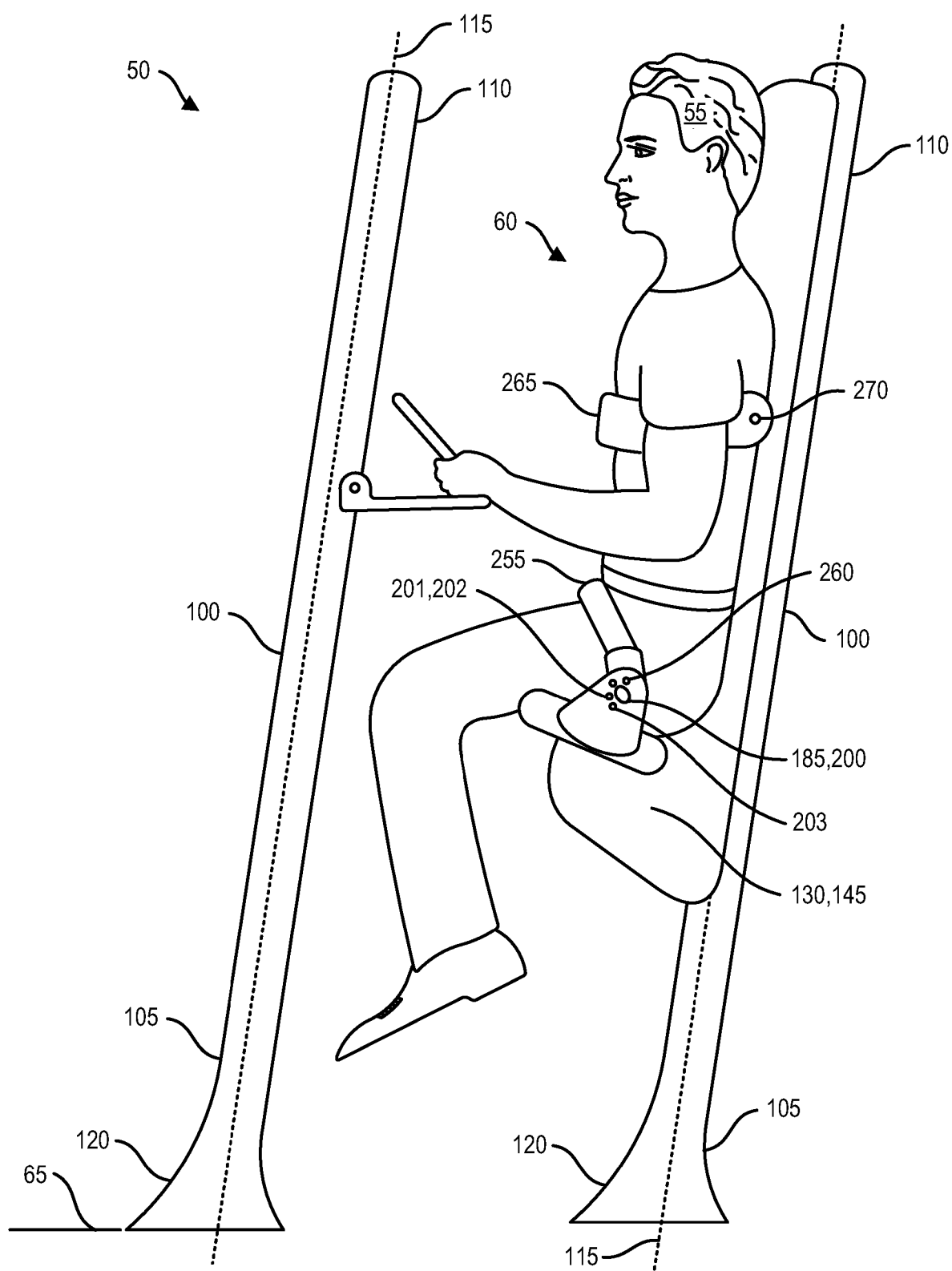
FIG. 5 shows a side elevation view of the external structural brace apparatus for supporting a user in a semi standing position on a surface that further includes a chest belt and a seat belt, plus shows a pair of the external structural brace apparatus is positional relation to one another on the surface with in addition the user shown in a knees up suspended seating position.

Further, FIG. 5 shows a side elevation view of the external structural brace apparatus 50 for supporting the user 55 in the semi standing position 60 on the surface 65 that further includes the chest belt 265 and the seat belt 255 plus shows the pair of the external structural brace apparatus 50 in positional relation to one another on the surface 65, in addition the user 55 is shown in a knees up suspended seating position.

Figure 6:
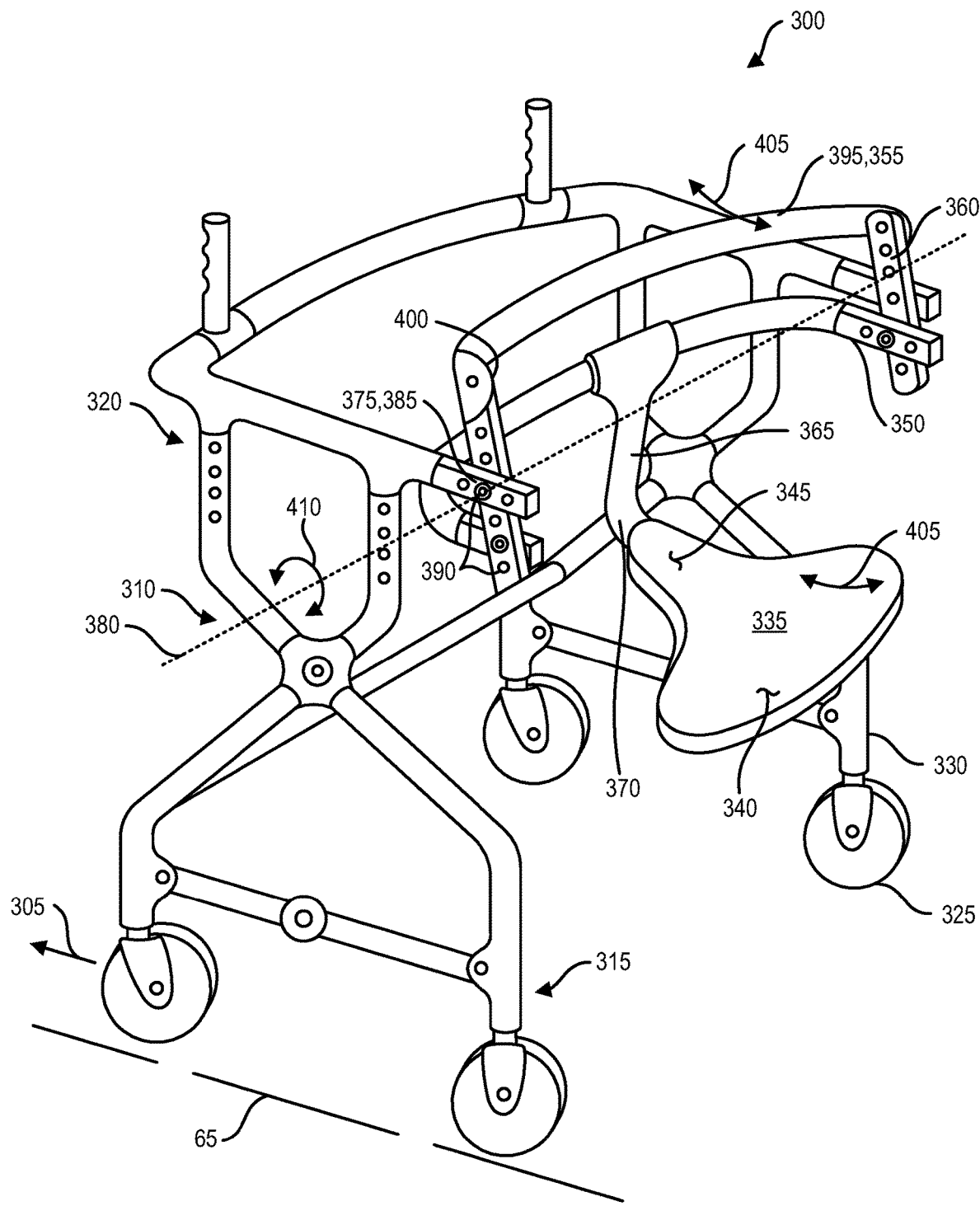
FIG. 6 shows an upper perspective view of a first alternative embodiment structural brace apparatus for supporting a user on a surface for the user to ambulate across the surface, the first alternative embodiment includes a frame structure, a means for ambulating across the surface, a rear mount saddle seat, and a torso support ring.

Next, FIG. 6 shows an upper perspective view of the first alternative embodiment structural brace apparatus 300 for supporting the user 55 on the surface 65 for the user 55 to ambulate 305 across the surface 65, the first alternative embodiment 300 includes the frame structure 310, the means 325 for ambulating 305 across the surface 65, the rear mount saddle seat 335, and the torso support ring 355. Next, FIG. 7 shows an upper perspective view of the first alternative embodiment structural brace apparatus 300 for supporting the user 55 on the surface 65 for the user 55 to ambulate 305 across the surface 65, the first alternative embodiment 300 includes the frame structure 310, the means 325 for ambulating 305 across the surface 65, the front mount saddle seat 335, and the torso support ring 355.

Figure 7:
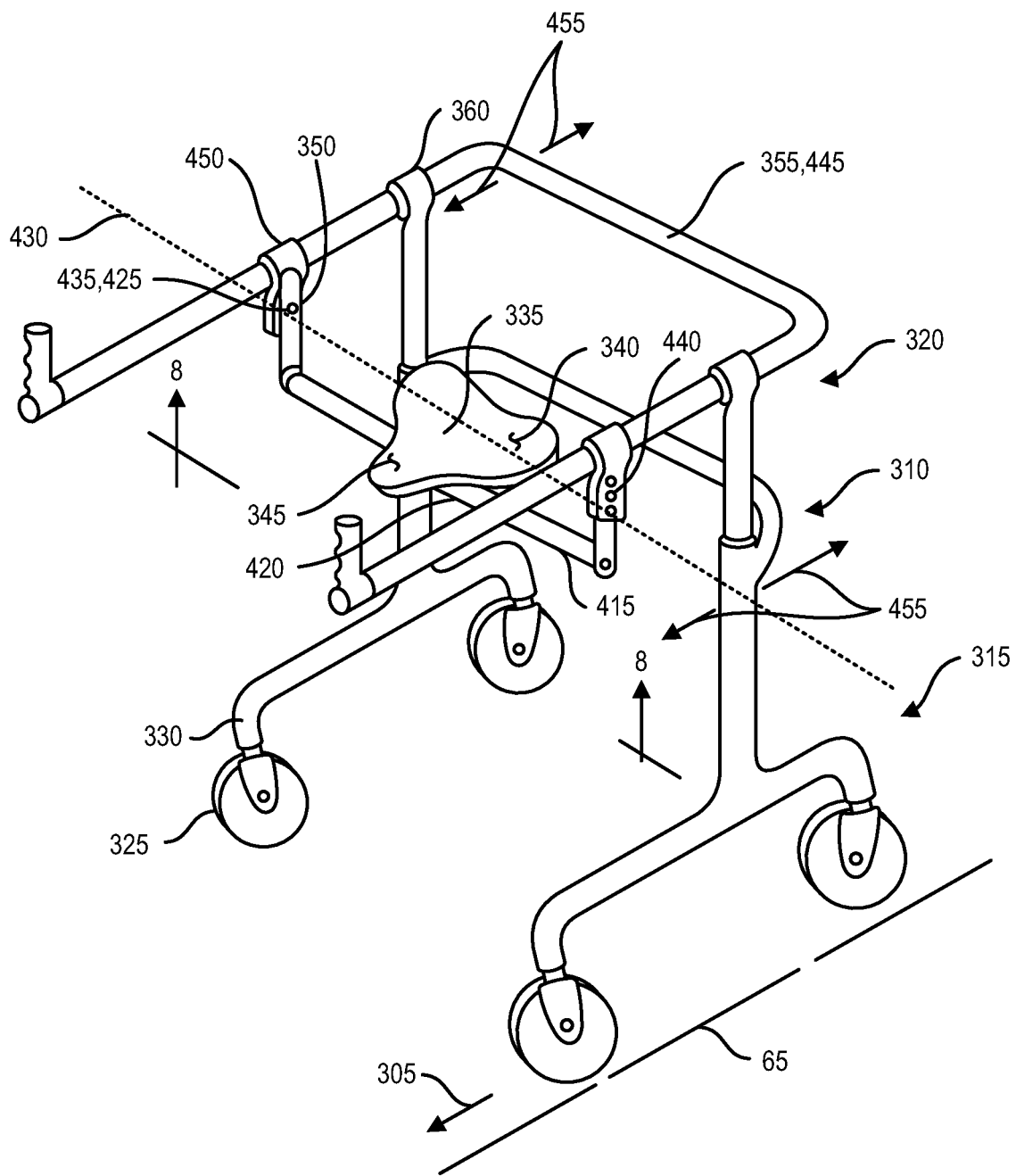
FIG. 7 shows an upper perspective view of a first alternative embodiment structural brace apparatus for supporting a user on a surface for the user to ambulate across the surface, the first alternative embodiment includes a frame structure, a means for ambulating across the surface, a front mount saddle seat, and a torso support ring.
Figure 8:
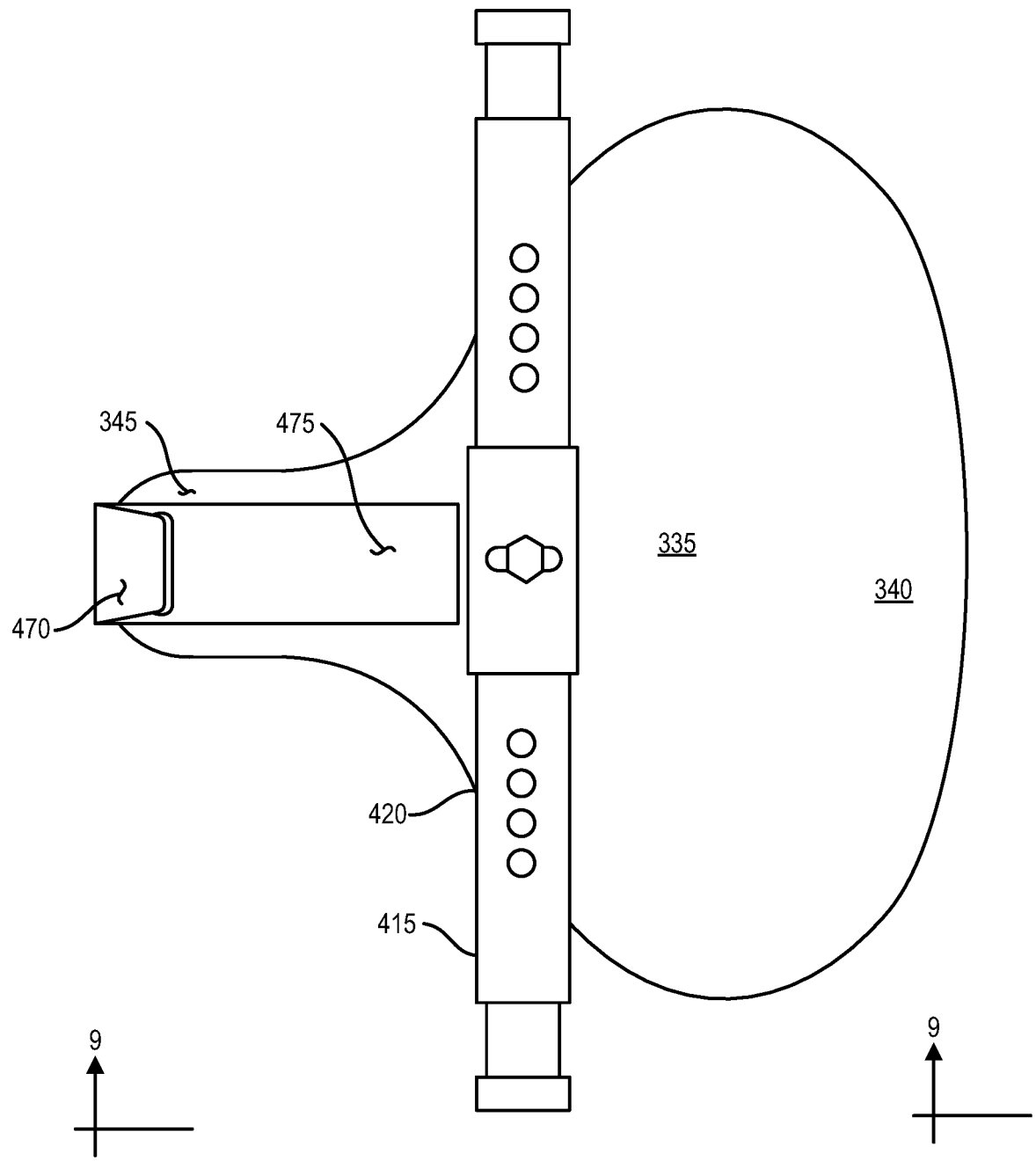
FIG. 8 shows view 8-8 from FIG. 7 of in particular the saddle seat mount for the front mount version that includes the saddle seat wide portion and the saddle seat midpoint narrow extension portion along with a retainer that is mounted on the midpoint narrow extension portion of the saddle seat.
Figure 9:
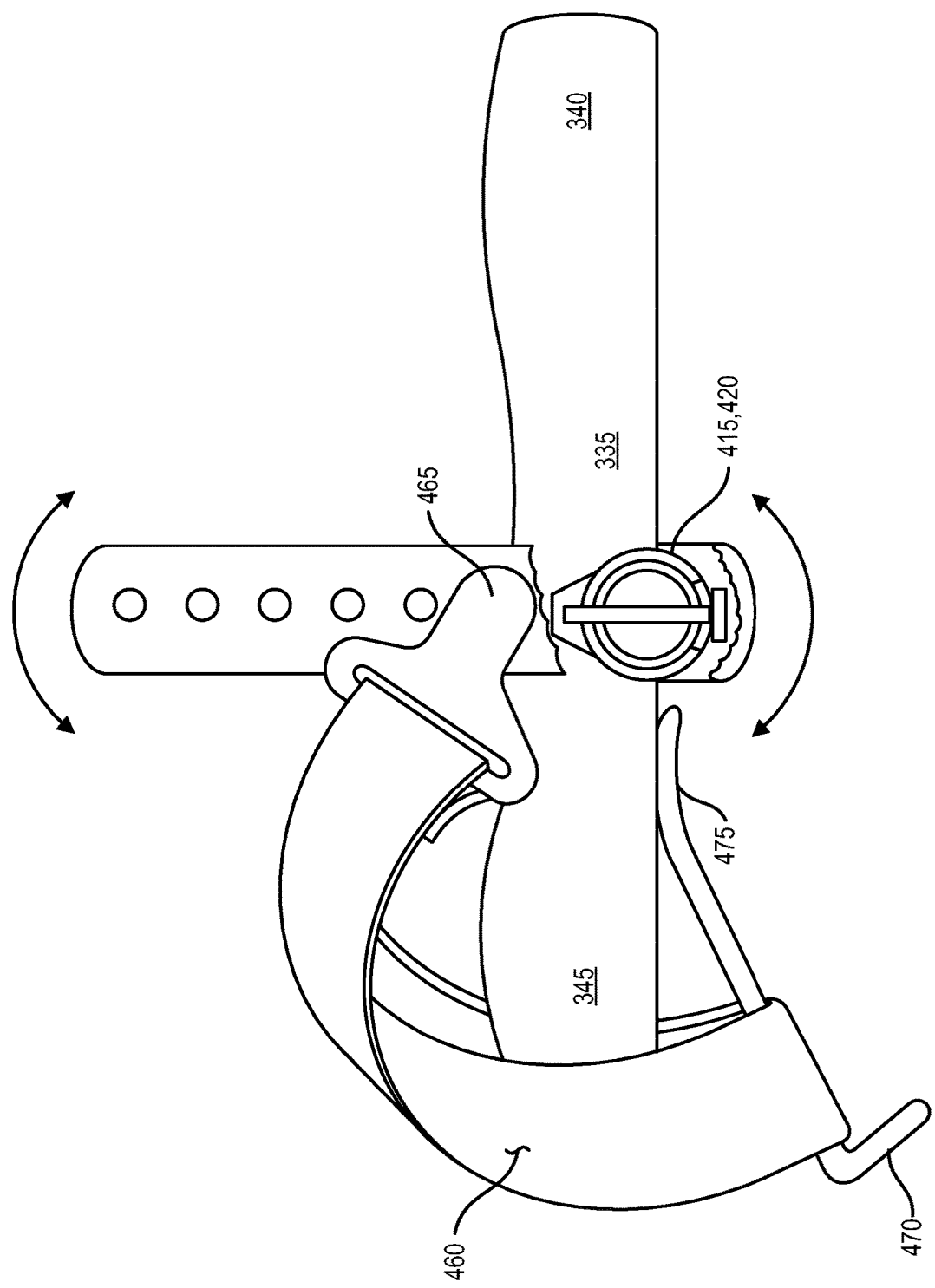
FIG. 9 shows a side elevation view of the saddle seat in FIG. 7, wherein FIG. 9 details the saddle seat, the saddle seat wide portion and the saddle seat midpoint narrow extension portion along the retainer that is mounted on the midpoint narrow extension portion of the saddle seat as shown holding the leg belt, further shown is the channel extension saddle seat mounting.

Further, FIG. 8 shows view 8-8 from FIG. 7 of in particular the saddle seat 335 mount 415 for the front mount version that includes the saddle seat 335 wide portion 340 and the saddle seat 335 midpoint narrow extension portion 345 along with the retainer 470 that is mounted 475 on the midpoint narrow extension portion 345 of the saddle seat 335. Continuing, FIG. 9 shows a side elevation view of the saddle 335 seat in FIG. 7, wherein FIG. 9 details the saddle seat 335, the saddle seat 335 wide portion 340 and the saddle seat midpoint narrow extension portion 345 along the retainer 470 that is mounted on the midpoint narrow extension portion 345 of the saddle seat 335 as shown holding the leg belt 460, further shown is the channel extension 415 saddle seat 335 mounting 420.

Figure 10:
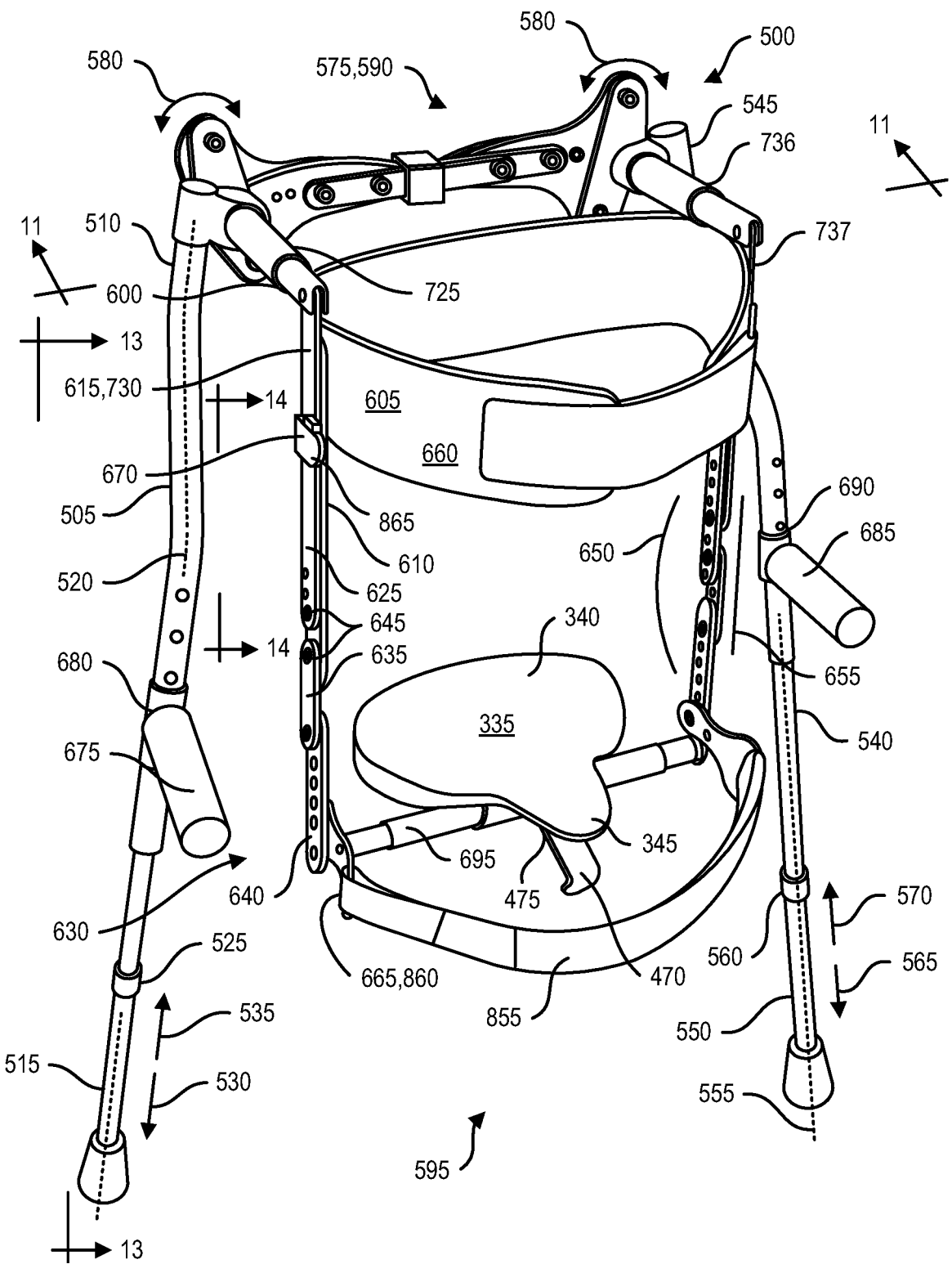
FIG. 10 shows an upper perspective view of a second alternative embodiment external structural brace apparatus for supporting a user on a surface for the user to ambulate along the surface with the second alternative embodiment including a first support extension strut, a second support extension strut, a mechanism disposed between the first and second struts for symmetrical and opposite primary pivotal movement as between struts, with a support structure, first and second handles, and a saddle seat.

Moving onward, FIG. 10 shows an upper perspective view of the second alternative embodiment external structural brace apparatus 500 for supporting the user 55 on the surface 65 for the user 55 to ambulate along the surface 65 with the second alternative embodiment 500 including the first support extension strut 505, the second support extension strut 540, the mechanism 590 disposed between the first 505 and second 540 struts for symmetrical and opposite primary pivotal movement 580 as between the struts 505, 540, with the support structure 595, first 675 and second 685 handles, and the saddle seat 335.

Figure 11:
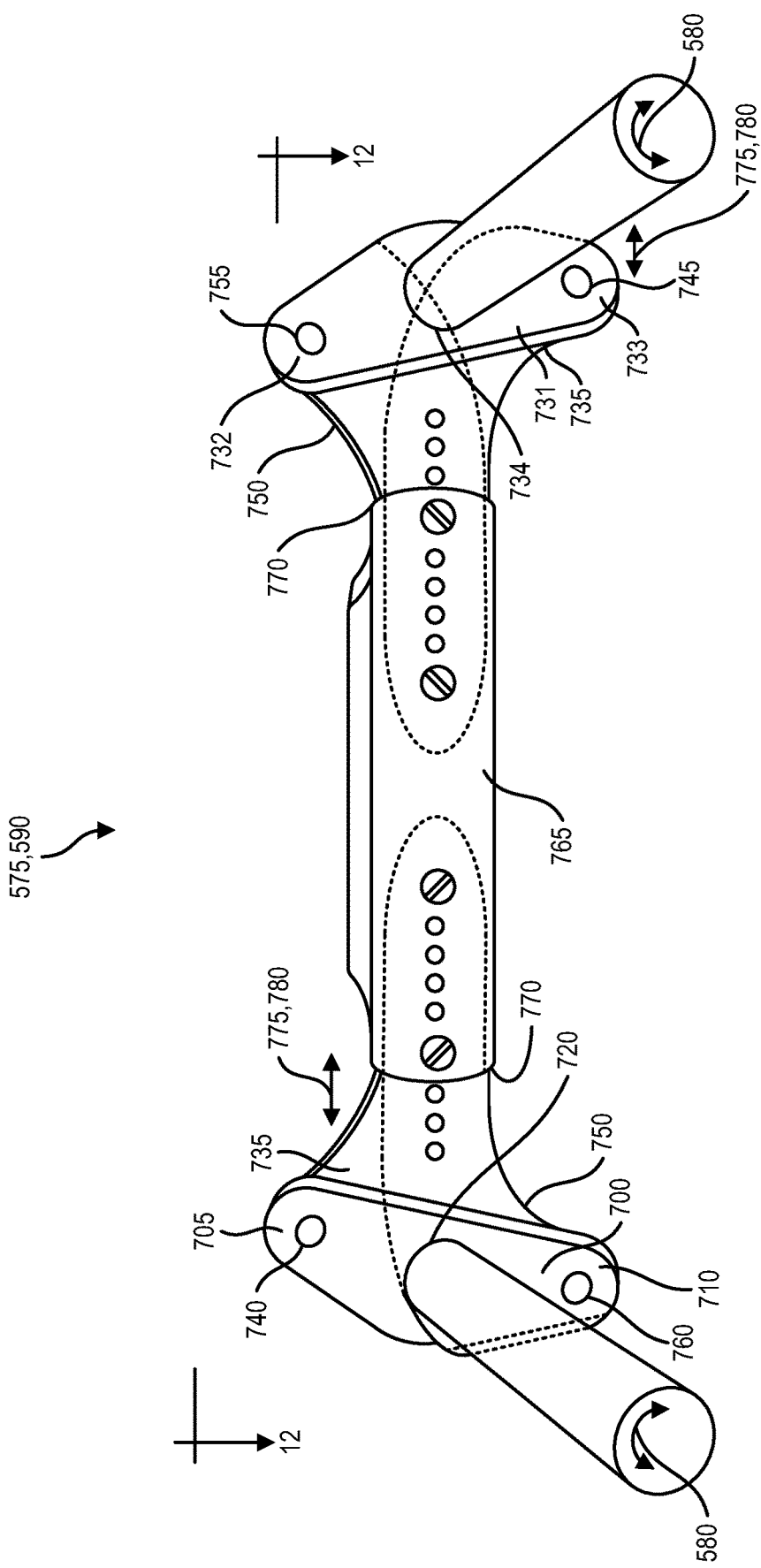
FIG. 11 shows view 11-11 from FIG. 10 showing specific detail on the mechanism that includes a first and second pivot bases each having primary and secondary end portions, first and second S shaped arms that are cross pivot connected to the first and second pivot bases wherein the first and second arms are oppositely slidably engaged to one another within a sheath, further shown are affixments of the first and second pivot bases to the first and second strut proximal end portions.

Next, FIG. 11 shows view 11-11 from FIG. 10 showing specific detail on the mechanism 590 that includes the first 700 and second 731 pivot bases each having primary 705, 710 and secondary 732, 733 end portions, first 735 and second 750 S shaped arms that are cross pivot connected to the first 700 and second 731 pivot bases wherein the first 735 and second 750 arms are oppositely slidably engaged 770 within the sheath 765, to one another, further shown is affixments 720, 734 of the first 700 and second 731 pivot bases to the first 510 and second 545 strut proximal end portions.

Figure 12:
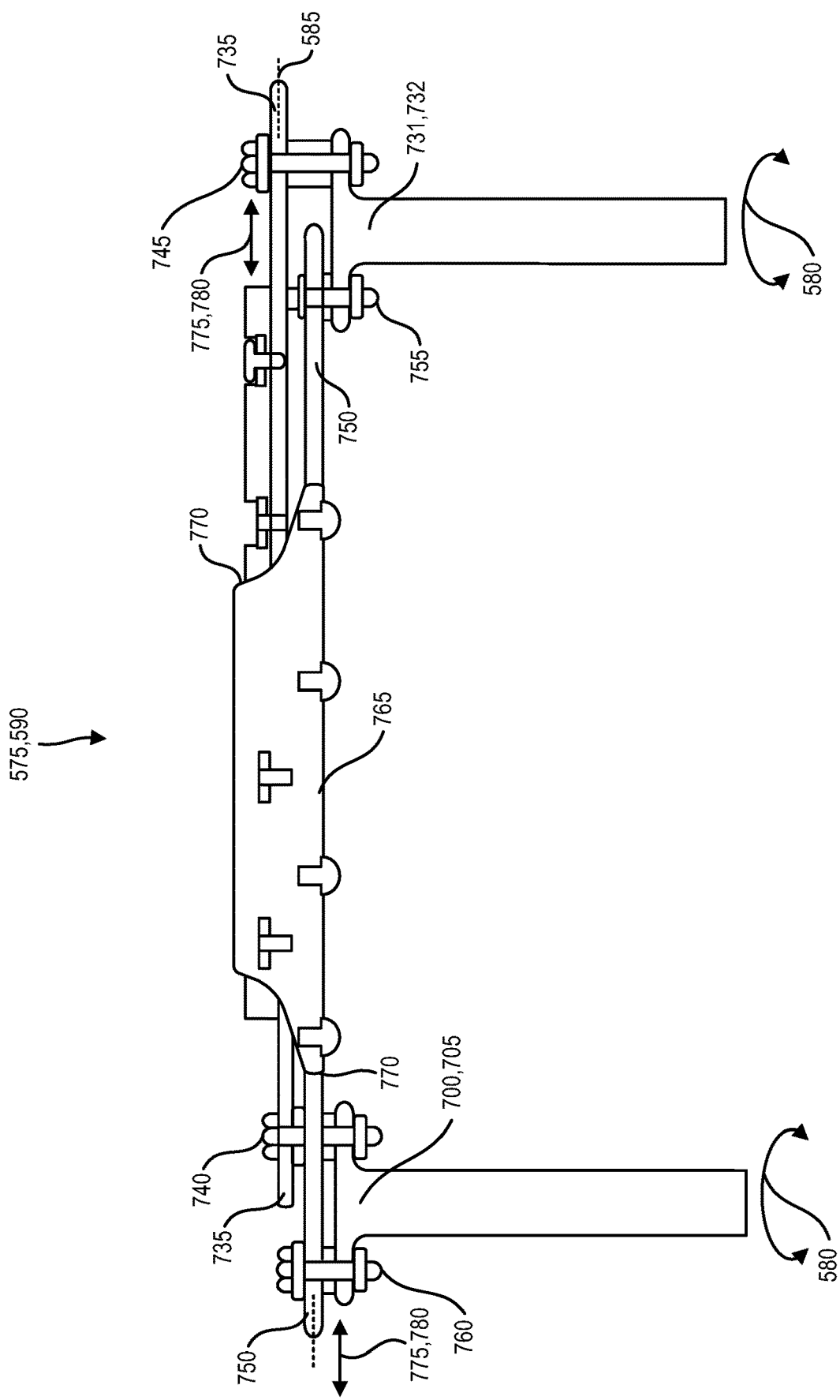
FIG. 12 shows view 12-12 from FIG. 11 which is a plan view of the mechanism that includes the first and second pivot bases each having primary and secondary end portions, the first and second S shaped arms that are cross pivot connected to the first and second pivot bases wherein the first and second arms are oppositely slidably engaged to one another within the sheath, further shown are the affixments of the first and second pivot bases to the first and second strut proximal end portions.

Continuing, FIG. 12 shows view 12-12 from FIG. 11 which is a plan view of the mechanism 590 that includes the first 700 and second 731 pivot bases each having primary 705, 710 and secondary 732, 733 end portions, the first 735 and second 750 S shaped arms that are cross pivot connected to the first 700 and second 731 pivot bases wherein the first 735 and second 750 arms are oppositely slidably engaged 770 within the sheath 765 to one another, further shown are the affixments 720, 734 of the first 700 and second 731 pivot bases to the first 510 and second 545 strut proximal end portions.

Figure 13:
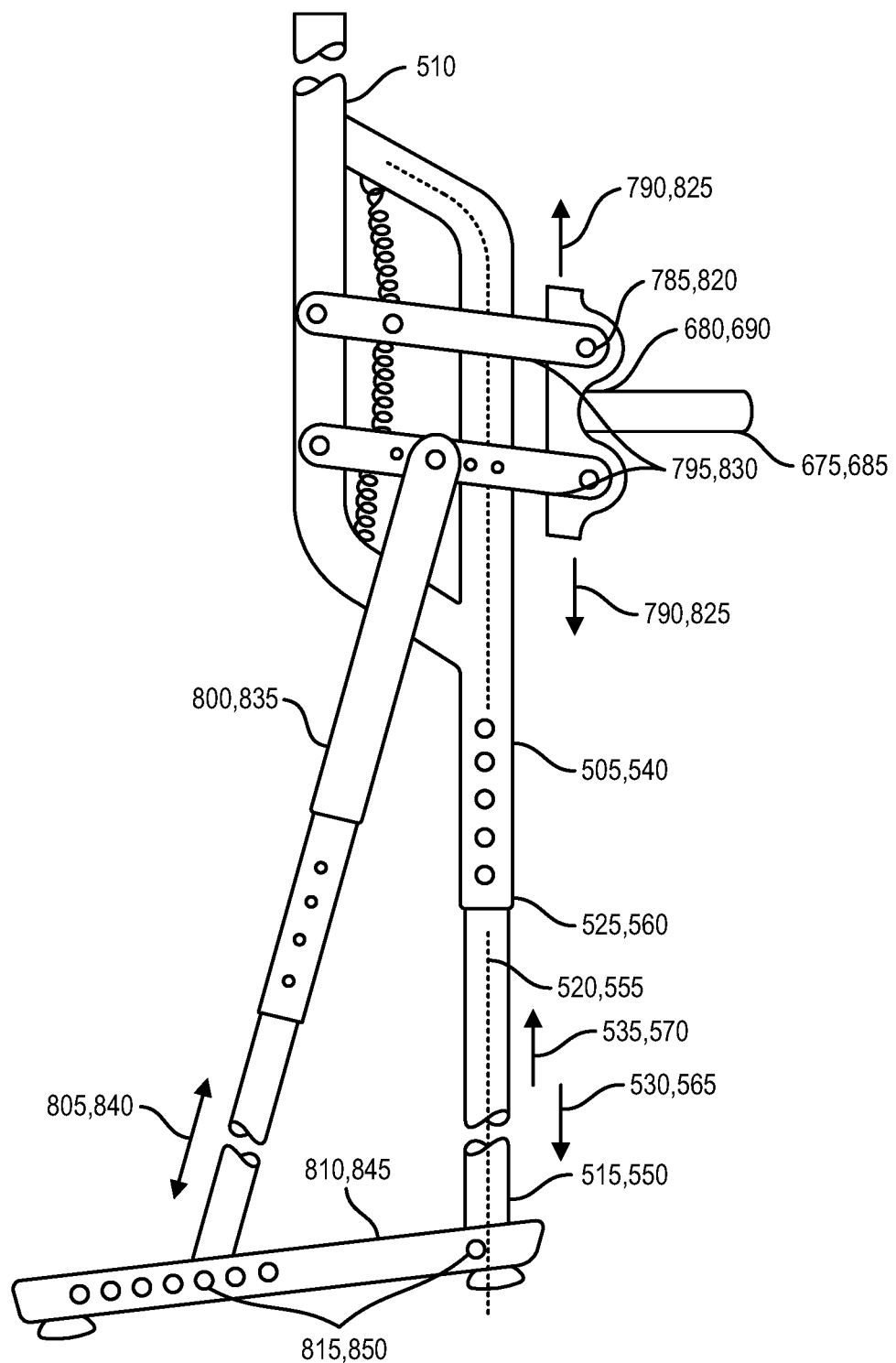
FIG. 13 shows view 13-13 from FIG. 10 showing in detail an elevation view of the first or second support extension struts with an option on the first or second handle structures that includes a pair of first or second pivotal links, ancillary first and second struts, first and second distal links, and the first and second telescoping cantilevers.
Figure 14:
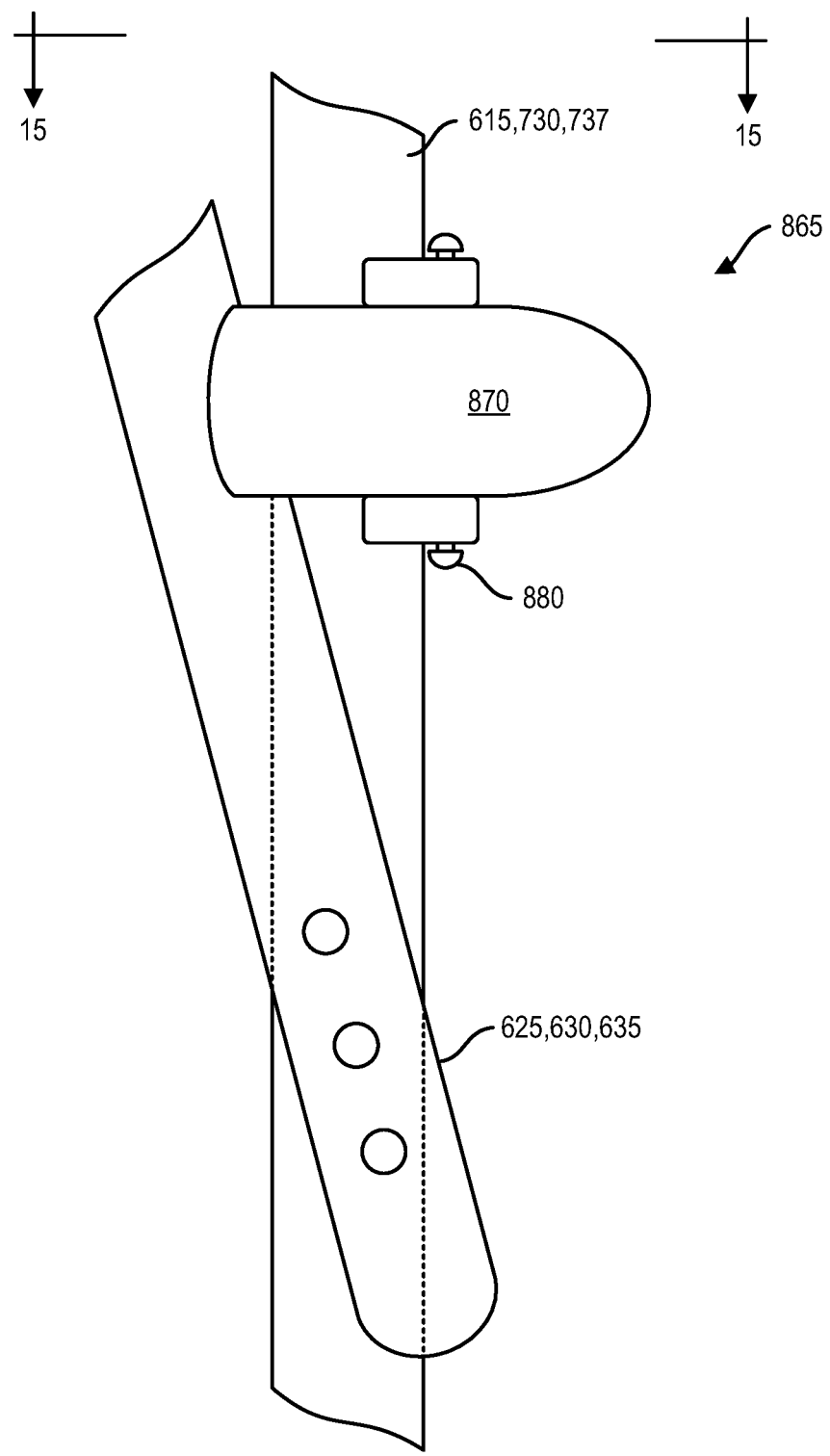
FIG. 14 shows view 14-14 from FIG. 10 that shows detail of a latch assembly that has a bar that is pivotally attached to either the first or second proximal extension ends wherein the bar removably engages a distal end portion of the extension element that is connected to a segmented links section.
Figure 15:
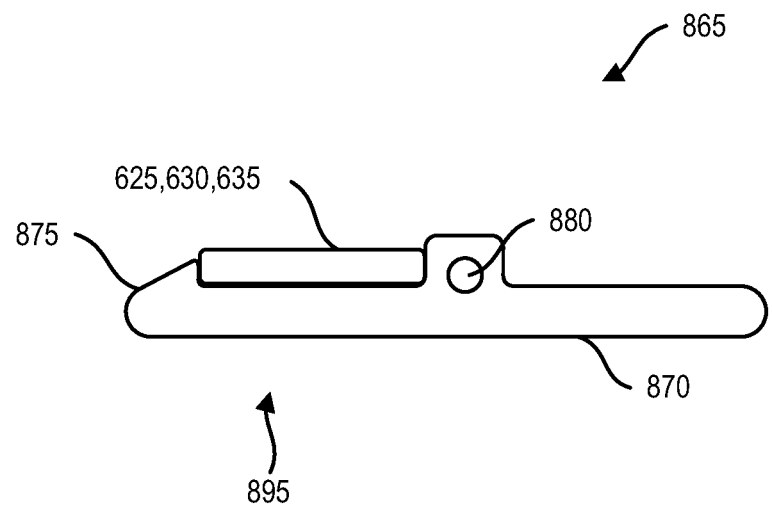
FIG. 15 shows view 15-15 from FIG. 14 of the latch assembly in both the open and closed states, showing the bar with a protrusion wherein the bar is pivotally attached to either the first or second proximal extension ends with a receiving channel, wherein the bar removably engages the distal end portion of the extension element that is connected to a segmented links section.
Figure 15:
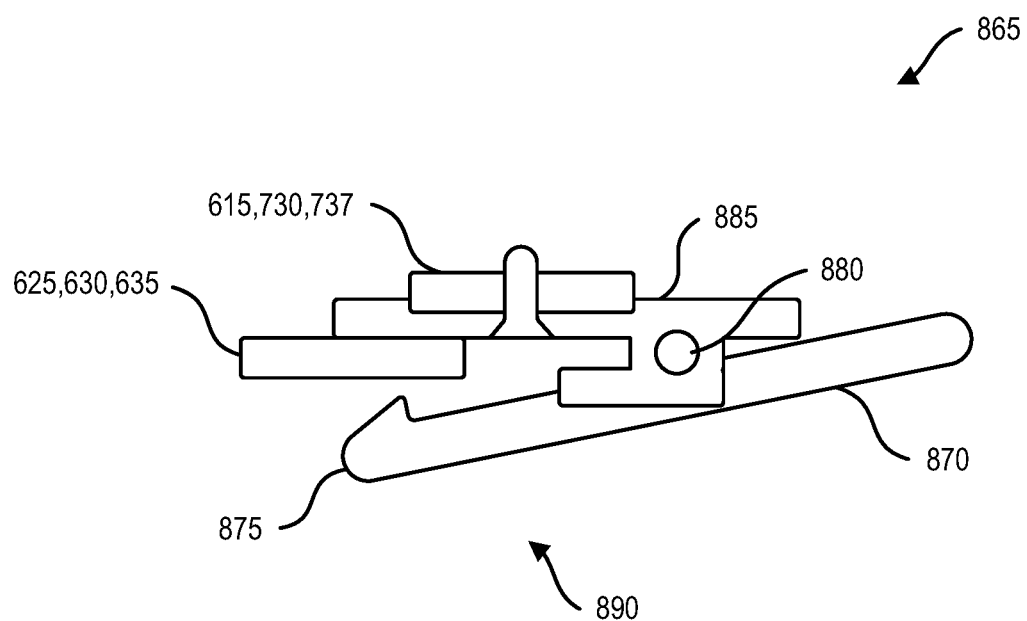

Next, FIG. 13 shows view 13-13 from FIG. 10 showing in detail an elevation view of the first 505 or second 540 support extension struts with an option on the first 675 or second 685 handle structures that includes the pair of first 795 or second 830 pivotal links, the ancillary first 800 and second 835 struts, the first 810 and second 845 distal links, and the first 525 and second 560 telescoping cantilevers. Also, FIG. 14 shows view 14-14 from FIG. 10 that shows detail of the latch assembly 865 that has a bar 870 that is pivotally attached 880 to either the first 730 or second 737 proximal extension ends wherein the bar 870 removably engages the distal end portion 625 of the extension element 610 that is connected to the segmented links section 630. Next, FIG. 15 shows view 15-15 from FIG. 14 of the latch assembly 865 in both the open 890 and closed 895 states, showing the bar 870 with the protrusion 875 wherein the bar 870 is pivotally attached 880 to either the first 730 or second 737 proximal extension ends with the receiving channel 885, wherein the bar 870 removably engages the distal end portion 625 of the extension element 610 that is connected to the segmented links section 630.

Broadly in looking specifically at FIGS. 1 to 5, the present invention is the external structural brace apparatus 50 for supporting the user 55 in the semi standing position 60 on the surface 65 to relieve shoulder, armpit, hand, foot, and wrist loads, the external structural brace apparatus 50 including the first support extension beam 70 having the first beam 70 proximal end portion 75 and the opposing first beam 70 distal end portion 80 and the first beam 70 longitudinal axis 85 spanning therebetween, see FIGS. 1, 4, and 5. The first beam 70 proximal end portion 75 is adapted to attach 90 to the surface 65, with the first support extension beam 70 including the first support structure 95 that is removably engagable to the first support extension beam 70 along the first longitudinal axis 85, as best shown in FIGS. 2 and 3.

Further included in the external structural brace apparatus is the second support extension beam 100 having the second beam 100 proximal end portion 105 and the opposing second beam 100 distal end portion 110 and the second beam longitudinal axis 115 spanning therebetween, the second beam 100 proximal end portion 105 is adapted to attach 120 to the surface 65, see FIGS. 1, 4, and 5, the second support extension beam 100 including the second support structure 125 that is removably engagable to the second support extension beam 100 along the second longitudinal axis 115, as best shown in FIGS. 2 and 3.

Also included in the external structural brace apparatus 50 is the channel 130 having the base 135 with the first leg 140 and the second leg 145, wherein the first 140 and second 145 legs each extend in the same direction from opposing sides of the base 135, the channel 130 extending lengthwise along the channel lengthwise axis 150, see FIGS. 1 and 2. The first leg 140 is affixed 155 to the first support structure 95 and the second leg 145 is affixed 160 to the second support structure 125 thereby positioning the first 85 and second 115 longitudinal axes substantially parallel 165 to one another, see FIGS. 1, 2, 4, and 5. Further the first 80 and second 110 beam distal end portions and the first 75 and second 105 beam proximal end portions are on matching ends from one another, see FIG. 1, wherein operationally the channel 130 can be positioned and locked 170 along the first 85 and second 115 longitudinal axes between the first 80 and second 110 beam distal end portions and the first 75 and second 105 beam proximal end portions, see FIGS. 1, 2, and 3.

In addition, included in the external structural brace apparatus 50 is the saddle seat 175 being generally planar with the midpoint substantially planar extension portion 180, the saddle 175 is attached 185 between the first 140 and second 145 legs and positioned such that the midpoint substantially planar extension 180 extends opposite of the channel 130 base 135, see FIGS. 1 and 2, wherein operationally the user 55 partially rests their buttocks on the saddle 175 and leans their back against the channel 130 base 135 to assume a semi supported standing posture 60, see FIGS. 4 and 5.

As an option for the external structural brace apparatus 50, wherein the saddle seat 175 attachment 185 between the first 140 and second 145 legs includes a first leg mechanism 190 and a second leg mechanism 195 to pivotally adjust and lock 200 the saddle 175 to the first 140 and second 145 legs about the saddle seat 175 pivotal axis 186, see in particular FIG. 2.

Another option for the external structural brace apparatus 50, wherein the first 95 and second 125 support structures are each constructed of respectively a first slot 205 disposed within the first support extension beam 70, with the first slot 205 running parallel 210 to the first longitudinal axis 85 with a mating first element 215 that has a first free slidable engagement 220 to the first slot 205, wherein the first element 215 has a first asymmetric locked slidable engagement 225 within the first slot 205 to selectively operationally lock 226 the first free slidable engagement 220, see in particular FIG. 3 and then FIG. 2. A second slot 230 disposed within the second support extension beam 100, with the second slot 230 running parallel 235 to the second longitudinal axis 115 with a mating second element 240 that has a second free slidable engagement 245 to the second slot 230, wherein the second element 240 has a second asymmetric locked slidable engagement 250 within the second slot 230 to selectively operationally lock 226 the second free slidable engagement 245, see in particular FIG. 3 and then FIG. 2.

A further option for the external structural brace apparatus 50, is adding a removably engagable seat belt 255 that is attached 260 to the first 140 and second 145 legs at saddle seat 175 attachments 185, see FIGS. 4 and 5, plus FIGS. 1 and 2. In addition, another option for the external structural brace apparatus 50, wherein it can further comprise a removably engagable chest belt 265 that is attached 270 to the first 140 and second 145 legs, see FIGS. 4 and 5.

Broadly in looking at FIGS. 6 to 9, the first alternative embodiment external structural brace apparatus 300 for supporting the user 55 on the surface 65 and for the user 55 to ambulate 305 along the surface 65 to relieve shoulder, armpit, hand, foot, and wrist loads, the first alternative embodiment external structural brace apparatus 300 includes the frame structure 310 having the first end portion 315 and the opposing second end portion 320, see FIGS. 6 and 7. Further included in the first alternative embodiment external structural brace apparatus 300 is the means 325 for ambulating 305 along the surface 65 that is attached 330 to the frame structure 310 first end portion 315, wherein preferably the means 325 is a pair of front castor wheels and a pair of rear fixed wheels, as best shown in FIGS. 6 and 7.

Also included in the first alternative embodiment external structural brace apparatus 300 is the saddle seat 335 being generally planar having the wide portion 340 and with the midpoint substantially planar narrow extension portion 345, the saddle seat 335 is attached 350 to the frame structure 310 second end portion 320, wherein operationally the saddle seat 335 facilitates the user 55 ambulating 305 along the surface 65 while seated in the saddle seat 335 with the user 55 facing the narrow extension portion 345 with the saddle seat 335 freeing legs of the user 55 for walking type movement, see FIGS. 6 and 7.

Further included in the first alternative embodiment external structural brace apparatus 300 is the torso support ring 355 affixed 360 to the frame structure 310 second end portion 320, wherein operationally the torso support ring 355 gives the user 55 a brace to apply force through their torso as against the frame structure 310 to help with stability and movement 305 along the surface 65 while the user 55 is ambulating 305 along the surface 65 while seated in the saddle seat 335, see FIGS. 6 and 7.

As an option for the first alternative embodiment external structural brace apparatus 300, wherein the saddle seat 335 being attached 350 to the frame structure 310 second end portion 320 is preferably constructed of an arcuate extension 365 emanating 370 from the saddle seat 335 narrow extension portion 345 to a first pivotal attachment 375 on the frame structure 310 second end portion 320, wherein the first pivotal attachment 375 is about a first pivotal axis 380, to operationally allow the user 55 to freely enter and sit upon the saddle seat 335 from the wide portion 340 side while having a first selectable pivot 385 and first surface height adjustment 390 of the saddle seat 335, see FIG. 6.

As another option for the first alternative embodiment external structural brace apparatus 300, wherein the torso support ring 355 is constructed of an arcuate band 395 that is affixed 400 to the first pivotal attachment 375 to operationally allow the arcuate band 395 to move in lockstep 405 with the saddle seat 335 in a first pivotal movement 410 about the first pivotal axis 380 for the user 55 to more easily push the frame structure 310 along the surface 65 with their torso while the user 55 is ambulating 305 along the surface 65 while seated in the saddle seat 335, see FIG. 6.

As a further option for the first alternative embodiment external structural brace apparatus 300, wherein the saddle seat 335 being attached 350 to the frame structure 310 second end portion 320 is constructed of a channel shaped extension 415 emanating 420 from between the saddle seat 335 narrow extension portion 345 and the saddle seat 335 wide portion 340 to a second pivotal attachment 425 on the frame structure 310 second end portion 320, wherein the second pivotal attachment 425 is about a second pivotal axis 430, to operationally allow the user 55 to freely enter and sit upon the saddle seat 335 from the saddle seat narrow extension portion 345 side while having a second selectable pivot 435 and second surface height adjustment 440 of the saddle seat 335, see FIG. 7.

In addition an option for the first alternative embodiment external structural brace apparatus 300, the torso support ring 355 is preferably constructed of an arcuate hoop 445 that is affixed 450 to the second pivotal attachment 425 to operationally allow the arcuate hoop 445 to move in lockstep 455 with the frame structure 310 for the user 55 to more easily rest their torso against the frame structure 310 while the user 55 is ambulating 305 along the surface 65 while seated in the saddle seat 335, see FIG. 7.

As an option for the first alternative embodiment external structural brace apparatus 300, wherein the saddle seat 335 can further comprise the leg belt 460 that is attached 465 to the channel shaped extension 415 and the retainer 470 disposed 475 on the narrow extension portion 345, wherein operationally the leg belt 460 helps secure the user 55 to the saddle seat 335 making it easier for the user 55 to ambulate 305 along the surface 65 while seated in the saddle seat 335, see in particular FIGS. 8 and 9, plus FIG. 7.

Broadly looking at FIGS. 10 to 15, the second alternative embodiment external structural brace apparatus 500 for supporting the user 55 on the surface 65 and for the user 55 to ambulate along the surface to relieve shoulder, armpit, hand, foot, and wrist loads, the second alternative embodiment external structural brace apparatus 500 includes the first support extension strut 505 having the first strut 505 proximal end portion 510 and the opposing first strut 505 distal end portion 515 and the first strut longitudinal axis 520 spanning therebetween, see FIG. 10. The first strut 505 distal end portion 515 including the first strut 505 telescoping cantilever strut 525 having extension 530 and retraction 535 movement along the first strut 505 longitudinal axis 520 to vary a total length of the first support extension strut 505, wherein the first telescoping cantilever strut 525 has intermittent contact with the surface, again see FIG. 10.

The second alternative embodiment external structural brace apparatus 500 also includes the second support extension strut 540 having the second strut 540 proximal end portion 545 and the opposing second strut 540 distal end portion 550 and the second strut 540 longitudinal axis 555 spanning therebetween, the second strut 540 distal end portion 550 including the second telescoping cantilever beam 560 having extension 565 and retraction 570 movement along the second strut 540 longitudinal axis 555 to vary a total length of the second strut support extension beam 540, see FIG. 10. Wherein the second strut telescoping cantilever beam 540 has intermittent contact with the surface, the first 510 and second 545 strut proximal end portions have the primary pivotal couple 575 to one another, wherein the first 505 and second 540 support extension struts are limited to have the primary pivotal movement 580 relative to one another in the single primary radial plane 585, see FIG. 10, plus FIGS. 11 and 12.

The second alternative embodiment external structural brace apparatus 500 additionally includes the mechanism 590 affixed therebetween the first 510 and second 545 strut proximal end portions that causes the primary pivotal movement 580 to be symmetrical as between the first 515 and second 550 strut distal end portions in equal and opposite directions, wherein a single primary pivotal movement 580 initiated at the first strut 505 distal end portion 515 causes an automatic equal and opposite primary pivotal movement 580 of the second strut 540 distal end portion 550 and a single primary pivotal movement 580 initiated at the second strut 540 distal end portion 550 causes an automatic equal and opposite primary pivotal movement 580 of the first strut 505 distal end portion 515, see FIG. 10, plus FIGS. 11 and 12.

The second alternative embodiment external structural brace apparatus 500 also includes the support structure 595 that has a connection 600 to the mechanism 590, wherein the support structure 595 is sized and configured 606 to removably engage an upper torso portion of the user, the support structure 595 having an extension element 610 with the proximal end 615 attached to the mechanism 590 and the distal end 625 pivotally attached 645 to a midpoint 635 of a segmented pivotal links section 630 that can be an arcuate shape 650 from a straight shape 655, see FIG. 10. The segmented pivotal links section 630 has one end attached 660 to a user's upper torso, and a lower end 640 attached 665 to a user's legs, to operationally facilitate such that a user can bend forward having support from the brace apparatus 500 wherein the segmented pivotal links section 630 is further lockable 670 for the user being in an upright position, see FIG. 10, plus FIGS. 14 and 15.

The second alternative embodiment external structural brace apparatus 500 also includes the first handle structure 675 disposed 680 upon the first strut 505 proximal end portion 510 and the second handle structure 685 disposed 690 upon the second strut 540 proximal end portion 545, again see FIG. 10. The second alternative embodiment external structural brace apparatus 500 also includes the saddle seat 335 being generally planar having the wide portion 340 and with the midpoint substantially planar narrow extension portion 345, the saddle seat 335 is attached 695 to the lower end 640 of the segmented pivotal links section 630, also see FIG. 10. Wherein operationally, the saddle seat 335 facilitates the user ambulating along the surface while seated in the saddle seat 335 with the user facing the narrow extension portion 345 with the saddle seat 335 freeing legs of the user for walking type movement with further stabilization by the torso engagement 605 and the first 505 and second 540 support extension struts, again see FIG. 10.

As an option for the second alternative embodiment external structural brace apparatus 500, wherein the mechanism 590 is constructed of the first pivot base 700 with the first pivot primary end portion 705 and the opposing first pivot secondary end portion 710, the first pivot base 700 is affixed 720 to the first strut 505 proximal end portion 510 and has the first rotational couple 725 to the first extension element proximal end 730 of the support structure 595, see FIGS. 11 and 12. Further included in the second alternative embodiment external structural brace apparatus 500 is the second pivot base 731 with the second pivot primary end portion 732 and the opposing second pivot secondary end portion 733, the second pivot base 731 is affixed 734 to the second strut proximal end portion 545 and has the second rotational couple 736 to the second extension element proximal end 737 of the support structure 595, see FIGS. 11 and 12.

As a continuing option for the second alternative embodiment external structural brace apparatus 500, the first S shaped arm 735 on one end has a first principal pivotal connection 740 to the first pivot primary end portion 705 and on another end of the first S shaped arm 735 the first dependent pivotal connection 745 to the second pivot secondary end portion 733, further the second S shaped arm 750 on one end has the second principal pivotal connection 755 to the second pivot primary end portion 732 and on another end of the second S shaped arm 750 a second dependent pivotal connection 760 to the first pivot secondary end portion 710, see FIGS. 11 and 12.

As another option for the second alternative embodiment external structural brace apparatus 500, the sheath 765 that is slidably engaged 770 to the first 735 and second 750 S shaped arms between the principal 740, 755 and dependent 745, 760 pivotal connections to operationally keep an opposing lateral movement 775 between the first 735 and second 750 S shaped arms substantially parallel 780, thus resulting in the primary pivotal movement 580 between the first 505 and second 540 support extension struts to be oppositely symmetric for increased stability of the user suspended via the support structure 595 in relation to the surface, see FIGS. 11 and 12, plus FIG. 10.

As a further option for the second alternative embodiment external structural brace apparatus 500, wherein the mechanism 590 first 700 and second 731 pivot bases plus the first 735 and second 750 S shaped arms are all preferably constructed of flat plate structures that are slidably engaged to one another at the first and second principal 740, 755 and dependent 745, 760 pivotal connections and the slidable engagement 770, as best shown in FIGS. 10, 11, and 12.

As an additional option for the second alternative embodiment external structural brace apparatus 500, wherein the first handle structure 675 that has the first handle pivotal engagement 785 on the first strut 505 proximal end portion 510, wherein the first handle pivotal engagement 785 has the first movement 790 along the first strut 505 longitudinal axis 520 through the pair of first pivotal links 795 to extend 805 or retract the ancillary first strut 800 that is pivotally linked 815 via a first distal link 810 to the first strut 505 distal end portion 515 that is operational to help boost the user forward motion to help the user ambulate across the surface, see in particular FIG. 13 and also FIG. 10.

As a further option for the second alternative embodiment external structural brace apparatus 500, wherein the second handle structure 685 that has the second handle pivotal engagement 820 on the second strut 540 proximal end portion 545, wherein the second handle pivotal engagement 820 has the second movement 825 along the second strut 540 longitudinal axis 555 through the pair of second pivotal links 830 to extend or retract 840 the ancillary second strut 835 that is pivotally linked 850 via the second distal link 845 to the second strut distal end portion 550 that is operational to help boost the user forward motion to help the user ambulate across the surface, see in particular FIG. 13 and also FIG. 10.

As an option for the second alternative embodiment external structural brace apparatus 500, wherein the segmented pivotal links 630 lower end 640 being attached to the user's legs is constructed of a leg belt 855 that is attached 860 to the segmented links lower end 640, see FIG. 10.

As another option for the second alternative embodiment external structural brace apparatus 500, the saddle seat 335 can further comprise the retainer 470 disposed 475 on the narrow extension portion 345 wherein the leg belt 855 is also held via the retainer 470 to operationally help secure the user to the saddle seat 335 making it easier for the user to ambulate along the surface while seated in the saddle seat 335, see FIG. 10 and further FIG. 9 as an example of the leg belt 855 routing from the first alternative embodiment 300.

A further option for the second alternative embodiment external structural brace apparatus 500, wherein the support structure 595 segmented pivotal links section 630 further comprises a latch 865 that removably engages between the extension element distal end 625 and the segmented pivotal links 630, to operationally facilitate the segmented pivotal links 630 straight shape 655 that can be selectively locked by the user, see FIGS. 14 and 15, plus FIG. 10.

As an ongoing option for the second alternative embodiment external structural brace apparatus 500, wherein the latch 865 is preferably constructed of the bar 870 with the end engaging protrusion 875 that has a bar 870 pivotal attachment 880 to a receiving channel 885 that is sized and configured to partially receive the extension element distal end 625 wherein the bar pivotal attachment 880 has a member that urges the bar 870 from the open state 890 toward the receiving channel 885 to be in the closed state 895 thereby securing the extension element distal end 625 into the receiving channel 885 to lock the straight shape 655 of the segmented pivotal links section 630, see FIGS. 14 and 15, plus FIG. 10.

CONCLUSION

Accordingly, the present invention of an external structural brace apparatus 50, first alternative embodiment 300, and the second alternative embodiment 500, have been described with some degree of particularity directed to the embodiments of the present invention. It should be appreciated, though; that the present invention is defined by the following claims construed in light of the prior art so that modifications or changes may be made to the exemplary embodiments of the present invention without departing from the inventive concepts contained therein.

The invention claimed is:

1. An external structural brace apparatus for supporting a user in a semi standing position fixed upon a surface to relieve shoulder, armpit, hand, foot, and wrist loads, said external structural brace apparatus comprising:
(a) a fixed first support extension beam having a first beam proximal end portion and an opposing first beam distal end portion and a first beam longitudinal axis spanning therebetween, said first beam proximal end portion is adapted to fixedly attach to the surface, said first support extension beam including a first support structure that is removably engagable to said first support extension beam along said first longitudinal axis;
(b) a fixed second support extension beam having a second beam proximal end portion and an opposing second beam distal end portion and a second beam longitudinal axis spanning therebetween, said second beam proximal end portion is adapted to fixedly attach to the surface, said second support extension beam including a second support structure that is removably engagable to said second support extension beam along said second longitudinal axis;
(c) a continuous channel having a base with a first leg and a second leg, wherein said first and second legs each extend in the same direction from opposing sides of said base, said channel continuously extending lengthwise along a channel lengthwise axis, said channel continuously extending from said first beam proximal end portion to said first beam distal end portion and from said second beam proximal end portion to said second beam distal end portion, said first leg is affixed to said first support structure and said second leg is affixed to said second support structure thereby positioning said first and second longitudinal axes substantially parallel to one another with said first and second beam distal end portions and said first and second beam proximal end portions on matching ends from one another, wherein operationally said channel can be positioned and locked along said first and second longitudinal axes between said first and second beam distal end portions and said first and second beam proximal end portions, wherein operationally said channel continuously extends to give the user support from their pelvis, to their lower back and upper back, to their shoulders, and to the back of their head; and
(d) a saddle seat being generally planar with a planar portion and with a midpoint substantially planar extension portion, said saddle seat has a free pivotal attachment about a saddle seat pivotal axis between said first and second legs and positioned such that said midpoint substantially planar extension portion extends opposite of said channel base, further wherein said saddle seat planar portion and planar extension portion are offset from said saddle seat pivotal axis, wherein said offset is positioned such that said saddle seat planar portion and planar extension portion are closer to said first and second proximal end portions of said first and second support extension beams than said saddle seat pivotal axis, wherein operationally the user partially rests their buttocks on said saddle and leans their back against said channel base to assume the semi standing position.

2. An external structural brace apparatus according to claim 1 wherein said saddle seat free pivotal attachment between said first and second legs includes a first leg mechanism and a second leg mechanism to pivotally adjust and lock said saddle to said first and second legs about said saddle seat pivotal axis.

3. An external structural brace apparatus according to claim 1 wherein said first and second support structures are each constructed of respectively a first straight slot disposed within said first support extension beam, with said first straight slot running parallel to said first longitudinal axis with a mating first eccentric element that is rotated into a first free slidable engagement to said first straight slot wherein said first eccentric element is subsequently rotated into ha; a first asymmetric locked slidable engagement within said first straight slot to selectively operationally lock said first slidable engagement, a second straight slot disposed within said second support extension beam, with said second straight slot running parallel to said second longitudinal axis with a mating second eccentric element that is rotated into a second free slidable engagement to said second straight slot wherein said second eccentric element is subsequently rotated into a second asymmetric locked slidable engagement within said second straight slot to selectively operationally lock said second slidable engagement.

4. An external structural brace apparatus according to claim 1 further comprising a removably engagable seat belt that is attached to said first and second legs saddle seat free pivotal attachment.

5. An external structural brace apparatus according to claim 4 further comprising a removably engagable chest belt that is attached to said first and second legs.

* * * * *